United States Patent
Araki et al.

(10) Patent No.: US 10,752,650 B2
(45) Date of Patent: Aug. 25, 2020

(54) SOPHOROLIPID COMPOUND AND COMPOSITION COMPRISING SAME

(71) Applicant: SARAYA CO., LTD., Osaka (JP)

(72) Inventors: Michiaki Araki, Kashiwara (JP); Yoshihiko Hirata, Kashiwara (JP)

(73) Assignee: Saraya Co., Ltd., Osaka-shi (JP)

(*) Notice: Subject to any disclaimer, the term of this patent is extended or adjusted under 35 U.S.C. 154(b) by 213 days.

(21) Appl. No.: 14/911,174

(22) PCT Filed: Aug. 6, 2014

(86) PCT No.: PCT/JP2014/070788
§ 371 (c)(1),
(2) Date: May 23, 2016

(87) PCT Pub. No.: WO2015/020114
PCT Pub. Date: Feb. 12, 2015

(65) Prior Publication Data
US 2016/0280733 A1    Sep. 29, 2016

(30) Foreign Application Priority Data

Aug. 9, 2013  (JP) ................ 2013-167171

(51) Int. Cl.
  *C07H 15/10*   (2006.01)
  *A61K 8/60*    (2006.01)
  (Continued)

(52) U.S. Cl.
  CPC .......... *C07H 15/10* (2013.01); *A21D 2/16* (2013.01); *A23L 2/52* (2013.01); *A23L 29/10* (2016.08);
  (Continued)

(58) Field of Classification Search
  None
  See application file for complete search history.

(56) References Cited

U.S. PATENT DOCUMENTS 5,756,471 A    5/1998   Hillion et al.
5,981,497 A    11/1999  Maingault
(Continued)

FOREIGN PATENT DOCUMENTS

EP    0499434 A1   8/1992
EP    2351847 A1   8/2011
(Continued)

OTHER PUBLICATIONS

Machine translation of WO 2013/129667 A1, obtained May 7, 2019; Original WO 2013/129667 A1 published 2013 (Year: 2013).*

U.S. Appl. No. 14/382,480, filed Sep. 2, 2014, Hirata et al.
U.S. Appl. No. 15/061,330, filed Mar. 4, 2016, Ito et al.
Davila et al., Identification and determination of individual sophorolipids in fermentation products by gradient elution high-performance liquid chromatography with evaporative light-scattering detection. J Chromatogr. Oct. 1, 1993;648(1):139-49.
PCT/JP2014/070788, Nov. 11, 2014, International Search Report and Written Opinion (in Japanese, with English translation).
(Continued)

*Primary Examiner* — Shaojia A Jiang
*Assistant Examiner* — Bahar Craigo
(74) *Attorney, Agent, or Firm* — Wolf, Greenfield & Sacks, P.C.

(57) ABSTRACT

The subject invention provides a novel SL that is widely applicable to various fields including food or beverages, cosmetics, pharmaceuticals, and quasi-drugs.
A sophorolipid compound represented by Formula (I) below:

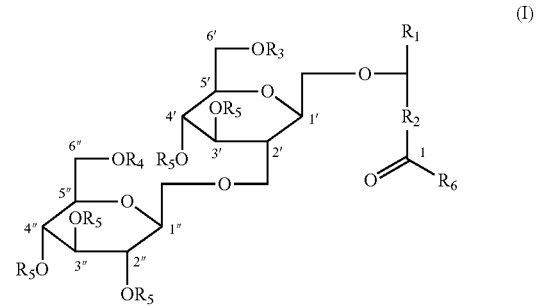

(in Formula (I), $R_1$ represents H or a methyl group; $R_3$ and $R_4$ each represents H or an acetyl group; one of five $R_5$ is a saturated or unsaturated fatty acid residue that may have an OH group, and the remaining four $R_5$ are H; $R_2$ represents a $C_{9-18}$ alkylene group, or $C_{9-18}$ alkenylene group having 1 to 3 double bonds; $R_6$ represents hydroxy, or may form a single bond together with one of five $R_7$ in the compound represented by Formula (II) below)

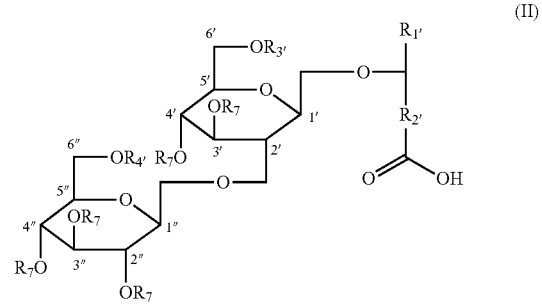

(in Formula (II), $R_{1'}$ represents H or methyl group; $R_{3'}$ and $R_{4'}$ each represents H or an acetyl group; $R_{2'}$ represents a $C_{9-18}$ alkylene group, or $C_{9-18}$ alkenylene group having 1 to 3 double bonds).

10 Claims, 17 Drawing Sheets

(51) Int. Cl.
       C07H 15/04      (2006.01)
       C07H 15/06      (2006.01)
       A21D 2/16       (2006.01)
       A23L 2/52       (2006.01)
       C12P 19/44      (2006.01)
       A61Q 19/00      (2006.01)
       A23L 29/10      (2016.01)
       A61Q 19/10      (2006.01)

(52) U.S. Cl.
       CPC .............. *A61K 8/602* (2013.01); *A61Q 19/00* (2013.01); *A61Q 19/007* (2013.01); *A61Q 19/10* (2013.01); *C07H 15/04* (2013.01); *C07H 15/06* (2013.01); *C12P 19/44* (2013.01); *C12P 19/445* (2013.01); *A23V 2002/00* (2013.01); *A61K 2800/10* (2013.01); *A61K 2800/40* (2013.01)

(56)                    References Cited

U.S. PATENT DOCUMENTS

| | | | |
|---|---|---|---|
| 6,057,302 | A | 5/2000 | Borzeix |
| 10,065,982 | B2 | 9/2018 | Hirata et al. |
| 2004/0171512 | A1 | 9/2004 | Furuta et al. |
| 2011/0237531 | A1* | 9/2011 | Yanagisawa ............ A61K 8/60 514/25 |
| 2012/0142621 | A1 | 6/2012 | Falus et al. |
| 2012/0220464 | A1 | 8/2012 | Giessler-Blank et al. |
| 2013/0035403 | A1 | 2/2013 | Schaffer et al. |
| 2015/0112049 | A1 | 4/2015 | Hirata et al. |
| 2016/0324747 | A1 | 11/2016 | Ito et al. |

FOREIGN PATENT DOCUMENTS

| | | | |
|---|---|---|---|
| JP | H07-118284 | A | 5/1995 |
| JP | H10-501260 | A | 2/1998 |
| JP | H11-508549 | A | 7/1999 |
| JP | 2002-045195 | A | 2/2002 |
| JP | 2003-009896 | | 1/2003 |
| JP | 2003-013093 | A | 1/2003 |
| JP | 2006-070231 | A | 3/2006 |
| JP | 2006-083238 | A | 3/2006 |
| JP | 2006-212086 | A | 8/2006 |
| JP | 2008-247845 | | 10/2008 |
| JP | 2009-062288 | | 3/2009 |
| JP | 2009-531310 | A | 9/2009 |
| JP | 2009-275145 | A | 11/2009 |
| JP | 2013-511266 | A | 4/2013 |
| WO | WO 2007/130738 | | 11/2007 |
| WO | WO 2010/050413 | A1 | 5/2010 |
| WO | WO 2011/061032 | A2 | 5/2011 |
| WO | WO 2011/127101 | A1 | 10/2011 |
| WO | WO 2013/129667 | A1 | 9/2013 |
| WO | WO2013/129667 | A1 * | 9/2013 |

OTHER PUBLICATIONS

PCT/JP2014/073356, Dec. 2, 2014, International Search Report and Written Opinion (in Japanese, with English translation of International Search Report only).
Extended European Search Report dated Nov. 16, 2016 for Application No. EP 14834955.8.
Ma et al., Effects of nitrogen sources on production and composition of sophorolipids by *Wickerhamiella domercqiae* var. sophorolipid CGMCC 1576. Appl Microbiol Biotechnol. Sep. 2011;91(6):1623-32. doi: 10.1007/s00253-011-3327-y.
Tulloch et al., Structure and reactions of lactonic and acidic sophorosides of 17-hydroxyoctadecanoic acid. Can J Chem. Feb. 1, 1968;46:3337-51.
EP 14834955.8, Nov. 16, 2016, Extended European Search Report.
[No Author Listed] Altern. Animal Test. Experiment, Guideline Draft. Dec. 1998;5(Supplement):1-3.
Okamoto, Recent developments of Draize eye test alternative in Japan. Fragrance Journal Feb. 2005;67-71.
Saerens et al., One-step production of unacetylated sophorolipids by an acetyltransferase negative Candida bombicola. Biotechnol Bioeng. Dec. 2011;108(12):2923-31. doi:10.1002/bit.23248. Epub Jul. 12, 2011.
Shah et al., Sophorolipids, microbial glycolipids with anti-human immunodeficiency virus and sperm-immobilizing activities. Antimicrob Agents Chemother. Oct. 2005;49(10):4093-100.
International Search Report and Written Opinion dated Nov. 11, 2014 for Application No. PCT/JP2014/070788.
International Search Report and Written Opinion dated Dec. 2, 2014 for Application No. PCT/JP2014/073356.
Ashby et al., Property control of sophorolipids: influence of fatty acid substrate and blending. Biotechnol Lett. Jun. 2008;30(6):1093-100. doi: 10.1007/s10529-008-9653-1. Epub Feb. 9, 2008.
Asmer et al., Microbial production, structure elucidation and bioconversion of sophorose lipids. J American Oil Chem Soc. Sep. 1988;65(9):1460-6.
Brakemeier et al., *Candida bombicola*: production of novel alkyl glycosides based on glucose/2-dodecanol. Appl Microbiol Biotechnol. 1998;50:161-6.
Cavalero et al., The effect of medium composition on the structure and physical state of sophorolipids produced by *Candida bombicola* ATCC 22214. J Biotech. 2003;103:31-41.
Cooper et al., Production of a Biosurfactant from Torulopsis bombicola. Appl Environ Microbiol. Jan. 1984;47(1):173-6.
Davila et al., Kinetics and balance of a fermentation free from product inhibition: sophorose lipid production by *Candida bombicola*. Appl Microbil Biotechnol. 1992;38:6-11.
Deshpande et al., Evaluation of sophorolipid biosurfactant production by *Candida bombicola* using animal fat. Bioresource Tech. 1995;54(2):143-150.
Gorin et al., Hydroxy Fatty Acid Glycosides of Sophorose from Torulopsis Magnoliae. Can J Chem. 1961;39(4):846-55.
Hirata et al., Natural synergism of acid and lactone type mixed sophorolipids in interfacial activities and cytotoxicities. Journal of Oleo Science, 2009, vol. 58, No. 9, pp. 565-572.
Hommel, Formation and physiological role of biosurfactants produced by hydrocarbon-utilizing microorganisms. Biosurfactants in hydrocarbon utilization. Biodegradation. 1990;1(2-3):107-19. Review.
Nuñez et al., LC/MS analysis and lipase modification of the sophorolipids produced by Rhodotorula bogoriensis. Biotechnol Lett. Jul. 2004;26(13):1087-93.
Tulloch et al., A new hydroxy fatty acid sophoroside from *Candida bogoriensis*. Can J Chem. Feb. 1, 1968;46(3):345-8.
Van Bogaert et al., Microbial production and application of sophorolipids. Appl Microbiol Biotechnol. Aug. 2007;76(1):23-34. Epub May 3, 2007. Review.
Zhou et al., Production of sophorose lipids by *Torulopsis bombicola* from safflower oil and glucose. J American Oil Chem Soc. Jan. 1992;69(1):89-91.
Daverey et al. Production, characterization, and properties of sophorolipids from the yeast *Candida bombicola* using a low-cost fermentative medium. Appl Biochem Biotechnol. Sep. 2009;158(3):663-74. doi: 10.1007/s12010-008-8449-z. Epub Dec. 10, 2008.
Zhou et al., Supramolecular assemblies of a naturally derived sophorolipid. Langmuir. Sep. 14, 2004;20(19):7926-32.
Daniel et al., Sophorolipid Production with High Yields on Whey Concentrate and Rapeseed Oil without Consumption of Lactose. Biotech Lett. Aug. 1998;20(8):805-807.
Examination Report for EP Application No. 148349558 dated Jul. 21, 2017.
Gu et al., A study of the scale-up of reversed-phase liquid chromatography. Separation Purification Tech. Jan. 4, 1999;15:41-58.
Rau et al., Sophorolipids: a source for novel compounds. Industrial Crops Products. Mar. 2001;13(2):85-92.
Shah et al., Utilization of restaurant waste oil as a precursor for sophorolipid production. Biotechnol Prog. Mar.-Apr. 2007;23(2):512-5. Epub Feb. 8, 2007.
Chinese Office Action dated Oct. 29, 2018 for Application No. CN 201480054091.5.

(56) References Cited

OTHER PUBLICATIONS

Liu et al., Progress on biosynthesis and application of sophorolipids. Food Drug. Nov. 2009;11(11):51-5.
Song et al., Structure characterization and physi-chemical properties of sophorolipid biosurfactants. Environmental Chemistry. Aug. 2011;30(8):1474-79.
Notice of Reasons for Refusal for Japanese Application No. 2018-568976 dated Jan. 22, 2019.
Third Party Observations for EP Application No. 14834955.8, dated Jun. 19, 2020.

* cited by examiner

SOPHOROLIPID COMPOUND AND COMPOSITION COMPRISING SAME

RELATED APPLICATIONS

The present application is a national stage filing under 35 U.S.C. § 371 of International PCT Application, PCT/JP2014/070788, filed Aug. 6, 2014, which claims priority to Japanese application 2013-167171, filed Aug. 9, 2013, each of which is incorporated herein by reference.

TECHNICAL FIELD

The present invention relates to a sophorolipid, which is a kind of biosurfactant.

BACKGROUND ART

Biosurfactants (hereinafter also referred to as BS), which are surfactants derived from living organisms, have high biodegradability and a high degree of safety, and are expected to be used industrially as next-generation surfactants.

A sophorolipid (hereinafter also referred to as SL), which is known as a glycolipid-type BS, is a fermentation product obtained from fermentation by yeast. An SL can be easily produced by, for example, inoculating yeast on a liquid medium containing carbon sources, such as sugars including glucose, and vegetable oils and fats, and stirring the medium while aerating the medium at a mild temperature and under pressure. Since SL has greater productivity (for example, about 100 g/L) than the other BS, it is widely used in industrial fields (Non-patent Document 1, Patent Document 1). Further, since SL is highly safe for the human body, SL has also been applied to detergents for dish-washing machines, and to cosmetics (Patent Document 2).

Further, in order to expand the application of SL, a great deal of research is currently being conducted, including concerning SL production by fermentation under different medium conditions (in particular, carbon sources) (Non-patent Documents 2 and 3), or chemical synthesis of SL derivatives (Patent Document 3).

However, there are general concerns regarding adverse environmental consequences or safety during the chemical synthesis of compounds. Nowadays, in view of LCA (Life-Cycle Assessment), the establishment of safer production methods, including raw material production, is recognized as important. Therefore, for the SL as well, which is derived from natural products and is thus considered highly safe, it is important to establish a production method that does not require the use and discharge of toxic organic solvents.

CITATION LIST

Patent Literature

Patent Document 1: JP2002-45195A
Patent Document 2: JP2003-13093A
Patent Document 3: JPH07-118284A

Non-Patent Document

Non-patent Document 1: Gorin, Can. J Chem., 39,846(1961)
Non-patent Document 2: A. Brakemeier, D. Wullbrandt, S. Lang, Appl Microbiol Biotechnol., 50, 161-166 (1998)
Non-patent Document 3: David A. Cavalero, David G. Cooper, Journal of Biotechnology 103 (2003) 31-41

SUMMARY OF INVENTION

Technical Problem

An object of the present invention is to provide a novel SL that is widely applicable to various fields including food or beverages, cosmetics, pharmaceuticals, and quasi-drugs. More specifically, an object of the present invention is to provide a novel SL that ensures surfactant performance to the same extent as that of conventional SL, and yet has significantly attenuated bitterness compared with conventional SL, and thus can be suitably used for food or beverages, cosmetics, and oral pharmaceuticals or quasi-drugs, without greatly impairing the taste thereof.

Solution to Problem

The present inventors have conducted thorough research in order to attain the above object, and, as a result, found that an SL compound with a novel structure different from conventional SL (acidic SL, lactonic SL) can be obtained from a culture of a microorganism having an SL-producing ability; and that the novel SL compound has surfactant performance (surface tension, emulsifying capacity) to the same extent as that of conventional SL (acidic SL, lactonic SL), and yet has significantly attenuated bitterness, unlike the bitter conventional SL. The SL compound is widely applicable as a component of, for example, food or beverages, oral pharmaceuticals, quasi-drugs, and cosmetics.

The present invention was developed based on the above findings, and includes the following embodiments.

(I) Novel Sophorolipid Compound (Novel SL Compound)

(I-1) an SL compound represented by Formula (I) below:

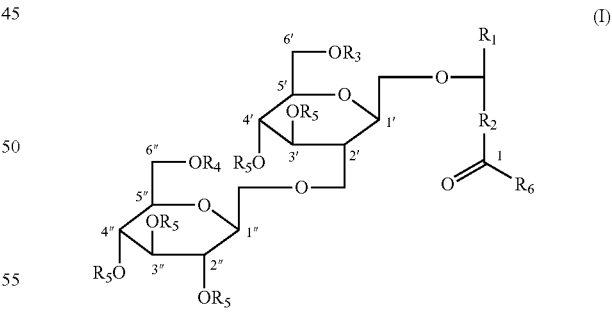

(in Formula (I), $R_1$ represents a hydrogen atom or methyl group; $R_3$ and $R_4$ are the same or different, and each represents a hydrogen atom or acetyl group; one of five $R_5$ is a saturated or unsaturated fatty acid residue that may have hydroxy, and the remaining four $R_5$ are all hydrogen atoms; $R_2$ represents a $C_{9-18}$ alkylene group, or $C_{9-18}$ alkenylene group having 1 to 3 double bonds; and $R_6$ represents hydroxy, or may form a single bond together with one of five $R_7$ in the compound represented by Formula (II) below;

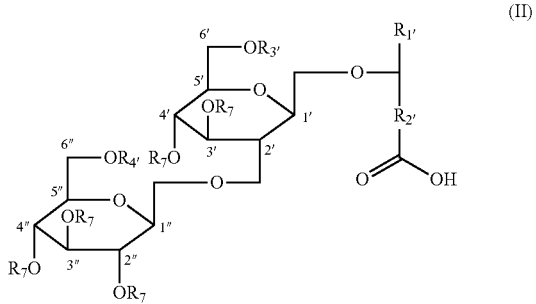

(in Formula (II), $R_{1'}$ represents a hydrogen atom or methyl group; $R_{3'}$ and $R_{4'}$ are the same or different, and each represents a hydrogen atom or acetyl group; $R_{2'}$ represents a $C_{9-18}$ alkylene group, or $C_{9-18}$ alkenylene group having 1 to 3 double bonds; and one of $R_7$ forms a single bond together with $R_6$ in the compound represented by Formula (I) and the remaining four $R_7$ are all hydrogen atoms)).

(I-2) The SL compound according to (I-1), wherein in Formula (I), one of $R_5$ of the $R_5O$-groups is a $C_{12-20}$ saturated fatty acid residue that may have hydroxy or $C_{12-20}$ unsaturated fatty acid residue that has 1 to 3 double bonds and that may have hydroxy; and the remaining $R_5$ are all hydrogen atoms.

(I-3) The SL compound according to (I-1) or (I-2), wherein the $R_5O$-group having $R_5$, which is a saturated or unsaturated fatty acid residue that may have hydroxy, is bonded at the 4"-position of the sophorose ring; and $R_5$ of the $R_5O$-groups bonded at the 3', 4', 2", and 3"-positions of the sophorose ring are all hydrogen atoms.

(I-4) The SL compound according to any one of (I-1) to (I-3), wherein in Formula (I), $R_6$ is a group represented by Formula (II); the $R_7O$-group having $R_7$, which forms a single bond together with $R_6$, is bonded at the 4"-position of the sophorose ring; and $R_7$ of the $R_7O$-groups bonded at the 3', 4', 2", and 3"-positions of the sophorose ring are all hydrogen atoms.

(I-5) The SL compound according to any one of (I-1) to (I-3), wherein in Formula (I), $R_6$ is hydroxy; $R_1$ is a methyl group; $R_2$ is a $C_{15}$ alkenylene group having one double bond; and $R_5$ of the $R_5O$-group bonded at the 4"-position of the sophorose ring is an oleic acid residue having hydroxy, and the remaining $R_5$ are all hydrogen atoms.

(I-6) The SL compound according to any one of (I-1) to (I-3), wherein in Formula (I), $R_6$ forms a single bond together with $R_7$ of the $R_7O$-group bonded at the 4"-position of the sophorose ring in Formula (II); $R_1$ is a methyl group; $R_2$ is a $C_{15}$ alkenylene group having one double bond; $R_5$ of the $R_5O$-group bonded at the 4"-position of the sophorose ring is an oleic acid residue having hydroxy, and the remaining $R_5$ are all hydrogen atoms; and, in Formula (II), $R_{1'}$ is a methyl group; and $R_{2'}$ is a $C_{13}$ alkylene group.

(I-7) The SL compound according to (I-1), wherein the SL compound is the compound specified in (1) or (2) below:
(1) in Formula (I), $R_6$ is hydroxy; $R_1$ is a methyl group; $R_2$ is a $C_{9-17}$ alkylene group or $C_{13-17}$ alkenylene group having 1 to 3 double bonds; $R_3$ and $R_4$ are the same or different, and each represents a hydrogen atom or acetyl group; $R_5$ of the $R_5O$-group bonded at the 4"-position of the sophorose ring is a $C_{12-20}$ fatty acid residue that may have or may not have hydroxy, and the remaining $R_5$ are hydrogen atoms; and
(2) in Formula (I), $R_6$ forms a single bond together with $R_7$ of the $R_7O$-group bonded at the 4"-position of the sophorose ring in Formula (II); $R_1$ is a methyl group; $R_2$ is a $C_{9-17}$ alkylene group, or $C_{13-17}$ alkenylene group having 1 to 3 double bonds; $R_3$ and $R_4$ are the same or different, and each represents a hydrogen atom or acetyl group; $R_5$ of the $R_5O$-group bonded at the 4"-position of the sophorose ring is a $C_{12-20}$ fatty acid residue that may have or may not have hydroxy, and the remaining $R_5$ are hydrogen atoms; and, in Formula (II), $R_{1'}$ is a methyl group; $R_{2'}$ is a $C_{9-17}$ alkylene group, or $C_{13-17}$ alkenylene group having 1 to 3 double bonds; and $R_{3'}$ and $R_{4'}$ are the same or different, and each represents a hydrogen atom or acetyl group.

(I-8) The SL compound according to (I-1), wherein the SL compound is a compound represented by Formula (III) or Formula (IV) below:

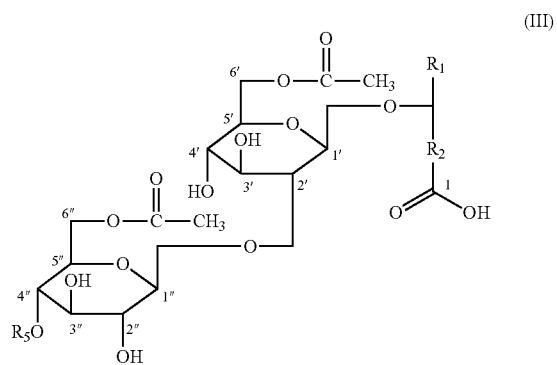

(in Formula (III), $R_1$ represents a methyl group, $R_2$ represents a $C_{15}$ alkenylene group, and $R_5$ represents an oleic acid residue having hydroxy)

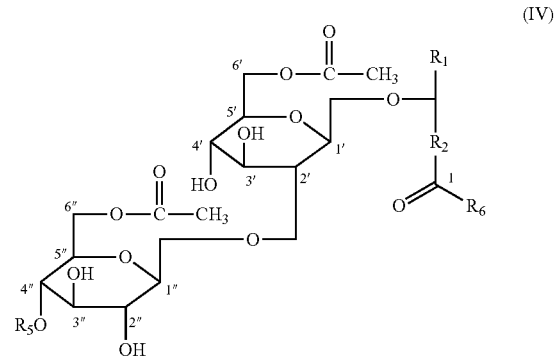

(in Formula (IV), $R_1$ represents a methyl group, $R_2$ represents a $C_{15}$ alkenylene group, $R_5$ represents an oleic acid residue having hydroxy, and $R_6$ forms a single bond together with $R_7$ in Formula (V) below)

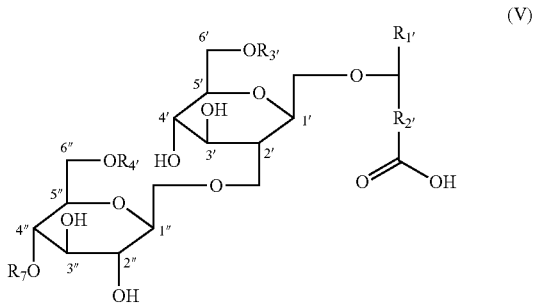

(V)

(in Formula (V), $R_{1'}$ represents a methyl group, $R_{2'}$ represents a $C_{13}$ alkylene group, $R_{3'}$ represents a hydrogen atom, and $R_{4'}$ represents an acetyl group).

(II) Composition Containing Novel Sophorolipid (II-1) A composition comprising at least one SL compound according to any one of (I-1) to (I-8). However, the composition does not include a culture of an SL-producing yeast.

(II-2) The composition according to (II-1), wherein the composition is a surfactant.

(II-3) The composition according to (II-1), wherein the composition is a pharmaceutical, a quasi-drug, a cosmetic, a food or beverage, or an additive thereof.

Advantageous Effects of Invention

The novel SL compound of the present invention has a surfactant performance (surface tension, emulsifying capacity) that is the same as or comparable to that of conventional SL (acidic SL, lactonic SL). On the other hand, the bitterness of the novel SL compound of the present invention is significantly attenuated compared with conventional SL, which has strong bitterness. Therefore, the novel SL compound of the present invention may be effectively used, with its interfacial activation effects, as a component (for example, emulsifier, antifoaming agent, coagulant, preservative, binder, stabilizer, and the like) of a product in fields, for example, food or beverages, oral pharmaceuticals, oral quasi-drugs, and cosmetics, in which conventional SL could not be applied or was applied only limitedly due to its bitterness.

By using the novel SL compound of the present invention, it becomes possible to impart a desirable surfactant performance to food or beverages, pharmaceuticals, quasi-drugs, and cosmetics, while hardly changing their taste.

BRIEF DESCRIPTION OF DRAWINGS

In FIG. 2, the peak around 3340 cm$^{-1}$ denoted by the dotted line with Reference Number 1 corresponds to OH stretching; the peaks around 2920 cm$^{-1}$ and 2850 cm$^{-1}$ denoted by the dotted lines with Reference Number 2 correspond to —CH$_2$, derived from methylene chain; the peak around 1740 cm$^{-1}$ denoted by the dotted line with Reference Number 3 corresponds to C═O, derived from carboxylic acid; the peak around 1240 cm$^{-1}$ denoted by the dotted line with Reference Number 4 corresponds to C═O, acetyl-derived carbonyl; and the peak around 1040 cm$^{-1}$ denoted by the dotted line with Reference Number 5 corresponds to C—O—H, derived from sugar.

Figure 1:
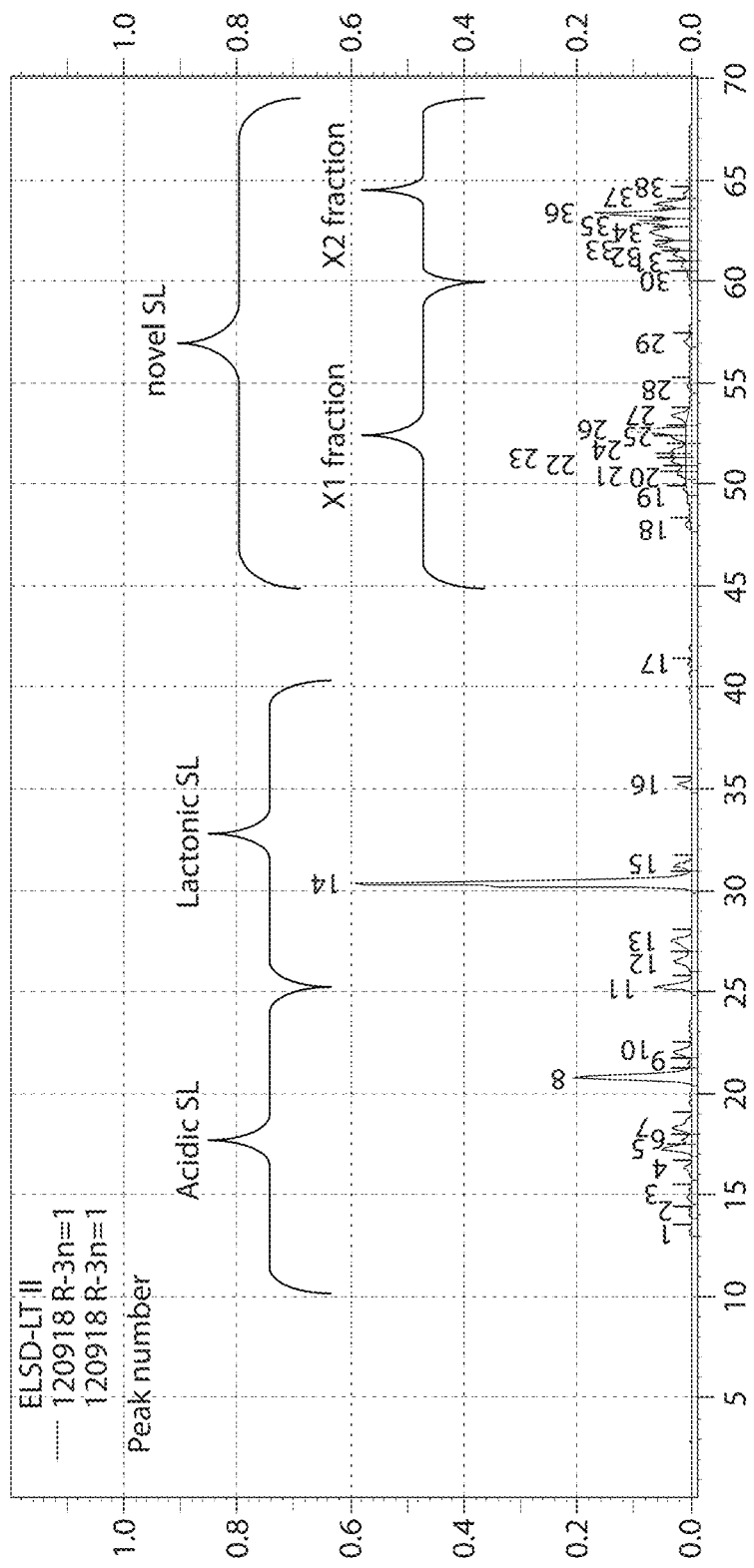
FIG. 1 shows a chromatogram obtained by reverse-phase column chromatography of a "conventional SL/novel SL-containing mixture" produced in Example 1(1) (see Example 1(3)).

DESCRIPTION OF EMBODIMENTS (I) Novel Sophorolipid Compound (Novel SL Compound)

The SL compound of the present invention (may hereinafter simply be referred to as "novel SL") may be represented by Formula (I) below.

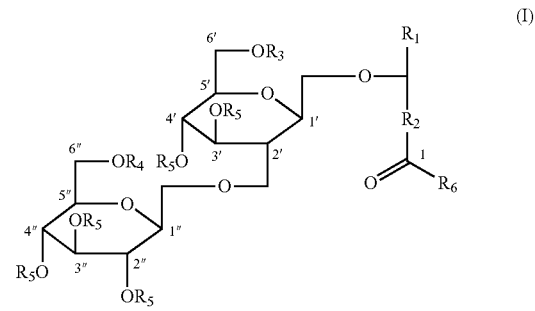

(I)

In Formula (I), $R_1$ represents a hydrogen atom or methyl group. $R_1$ is preferably a methyl group.

$R_3$ and $R_4$ are the same or different, and each represents a hydrogen atom or acetyl group. $R_3$ and $R_4$ may both be hydrogen atoms or acetyl groups. Further, when $R_3$ is a hydrogen atom, $R_4$ may be an acetyl group; conversely, when $R_3$ is an acetyl group, $R_4$ may be a hydrogen atom. $R_3$ and $R_4$ are preferably both acetyl groups.

$R_2$ is a $C_{9-18}$, preferably $C_{9-12}$ alkylene group, or a $C_{9-18}$, preferably $C_{13-18}$ alkenylene group having 1 to 3 double bonds. The $C_{9-18}$ alkylene group includes $C_{9-18}$ linear or branched alkylene groups, and is preferably a linear alkylene group. The number of carbon atoms is preferably 11 to 18, more preferably 13 to 18, particularly preferably 15 to 16. Further, the $C_{9-18}$ alkenylene group having 1 to 3 double bonds includes $C_{9-18}$ linear or branched alkenylene groups having 1 to 3 double bonds, and is preferably a linear alkenylene group, more preferably a $C_{9-18}$ linear alkenylene group having 1 or 2 double bonds, further preferably a $C_{9-18}$ linear alkenylene group having one double bond. The number of carbon atoms is preferably 13 to 18, more preferably 13 to 17, particularly preferably 13 to 16. $R_2$ is preferably a $C_{13-16}$ alkylene group or a $C_{13-16}$ alkenylene group having 1 or 2 double bonds, and more preferably a $C_{15-16}$ alkenylene group having one double bond.

$R_5$ represents a hydrogen atom, or a saturated or unsaturated fatty acid residue that may have hydroxy. One of five $R_5$ in the compound of Formula (I) (hereinafter may also be referred to as "Compound (I)") is a saturated or unsaturated fatty acid residue that may have hydroxy, and the remainder are all hydrogen atoms.

Examples of saturated fatty acid residues include $C_{12-20}$ linear fatty acid residues (lauric acid residue, myristic acid residue, pentadecylic acid residue, palmitic acid residue, margaric acid residue, stearic acid residue, arachidic acid residue), preferably $C_{14-20}$, more preferably $C_{16-20}$, further preferably $C_{16-13}$ linear fatty acid residue, and particularly preferably $C_{16}$ palmitic acid residue and $C_{18}$ stearic acid residue.

Further, examples of unsaturated fatty acid residues include $C_{12-20}$ linear fatty acid residues having 1 to 3 double bonds. The number of double bonds is preferably 1 to 2, more preferably 1. The number of carbon atoms is preferably 16 to 20, more preferably 16 to 18, particularly preferably 18. Preferable examples of unsaturated fatty acid residues include a $C_{16}$ palmitoleic acid residue having one double bond; a $C_{18}$ oleic acid residue or vaccenic acid residue having one double bond (preferably oleic acid residue); a $C_{18}$ linoleic acid residue having 2 double bonds; a $C_{18}$ linolenic acid residue (9,12,15), linolenic acid residue (6,9,12), and eleostearic acid residue having three double bonds; and a $C_{20}$ linolenic acid residue (9,12,15), linolenic acid residue (6,9,12), and eleostearic acid residue having 3 double bonds. More preferably, the unsaturated fatty acid residue is a $C_{16}$ palmitoleic acid residue having one double bond and a $C_{18}$ oleic acid residue having one double bond, particularly preferably a $C_{18}$ oleic acid residue having one double bond.

These fatty acid residues may have hydroxy, and may not have hydroxy. When the fatty acid residues have hydroxy, the number of hydroxy is 1 or 2, preferably 1. Further, the hydroxy may be present, for example, at co-position or ω-1-position in the fatty acid residue.

In Compound (I), when $R_5$ is a saturated or unsaturated fatty acid residue that may have hydroxy, —$OR_5$ may be present at any of the 3', 4', 2", 3", and 4"-positions of the sophorose ring. More specifically, Compound (I) of the present invention include an SL compound in which an —$OR_5$ group having $R_5$, which is the above-specified fatty acid residue, is present at at least one of these positions. More preferably, Compound (I) is a compound in which —$OR_5$ having $R_5$, which is a saturated or unsaturated fatty acid residue that may have hydroxy, is present at the 4"-position of the sophorose ring.

In Formula (I), $R_6$ may be hydroxy. For convenience, the SL compound of the present invention wherein $R_6$ is hydroxy may also be referred to as "a monomeric SL compound."

Further, $R_6$ in Formula (I) may form a single bond together with one of $R_7$ bonded at the 3', 4', 2", 3", or 4"-position of the sophorose ring of the molecule represented by Formula (II) through an ester bond.

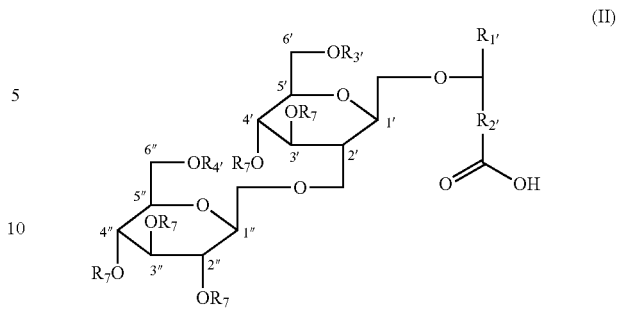

The $R_7$ that forms a single bond together with $R_6$ may be any of $R_7$ bonded at the 3', 4', 2", 3", or 4"-position of the sophorose ring in Formula (II). More specifically, Compound (I) of the present invention includes a dimer-form SL compound in which the compound represented by Formula (I) is bonded to one of $R_7$ through a bond with $R_6$ (single bond). Preferable examples of such a dimer-form SL compound includes a compound in which $R_7$ in —$OR_7$ at the 4"-position of the sophorose ring in Formula (II) forms a single bond together with $R_6$ in Formula (I). For convenience, to differentiate the dimer-form SL compound from the "monomeric SL compound" mentioned above, the dimer-form SL compound may also be referred to as a "dimeric SL compound."

In Formula (II), $R_{1'}$ represents a hydrogen atom or methyl group, preferably a methyl group.

$R_{3'}$ and $R_{4'}$ are the same or different, and each represents a hydrogen atom or acetyl group. $R_{3'}$ and $R_{4'}$ may both be hydrogen atoms, or may both be acetyl groups. Further, when $R_{3'}$ is a hydrogen atom, $R_{4'}$ may be an acetyl group; conversely, when $R_{3'}$ is an acetyl group, $R_{4'}$ may be a hydrogen atom. It is preferable that $R_{3'}$ is a hydrogen atom, and $R_{4'}$ is an acetyl group.

$R_{2'}$ represents a $C_{9-18}$, preferably $C_{9-17}$ alkylene group, or a $C_{9-18}$, preferably a $C_{13-18}$ alkenylene group having 1 to 3 double bonds. The $C_{9-18}$ alkylene group includes $C_{9-18}$ linear or branched alkylene groups, and is preferably a linear alkylene group. The number of carbon atoms is preferably 11 to 18, more preferably 13 to 18, further preferably 13 to 16, particularly preferably 13 or 14. Further, the $C_{9-18}$ alkenylene group having 1 to 3 double bonds includes $C_{9-18}$ linear or branched alkenylene groups having 1 to 3 double bonds, and is preferably a linear alkenylene group, more preferably a $C_{9-18}$ linear alkenylene group having 1 or 2 double bonds, further preferably a $C_{9-18}$ linear alkenylene group having one double bond. The number of carbon atoms is preferably 13 to 18, preferably 13 to 17, and particularly preferably 13 to 16. $R_{2'}$ is preferably a $C_{13-16}$ alkylene group or a $C_{13-16}$ alkenylene group having one double bond, and more preferably a $C_{13}$ or $C_{14}$ alkylene group.

When $R_6$ is a group represented by Formula (II), $R_2$ in Formula (I) and $R_{2'}$ in Formula (II) may be the same or different. When they are different, for example, $R_2$ is a $C_{15}$ alkenylene group having one double bond, and $R_{2'}$ is a $C_{13}$ alkylene group.

Preferable examples of the monomeric SL compound of the present invention include the compound represented by Formula (III) below, and preferable examples of the dimeric SL compound of the present invention include the compound represented by Formula (IV) below.

An Example of the Monomeric SL Compound (Referred to as "Novel SL (X1-26)" in the Examples)

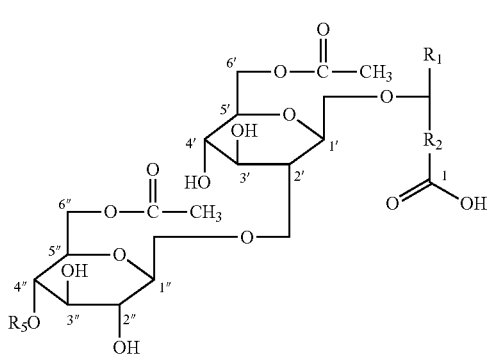

(III)

In Formula (III), $R_1$ represents a methyl group.

$R_2$ represents a $C_{15}$ alkenylene group having one double bond, and $R_5$ represents an oleic acid residue having hydroxy.

An Example of Dimeric SL Compound (Referred to as "Novel SL (X2-36)" in the Examples)

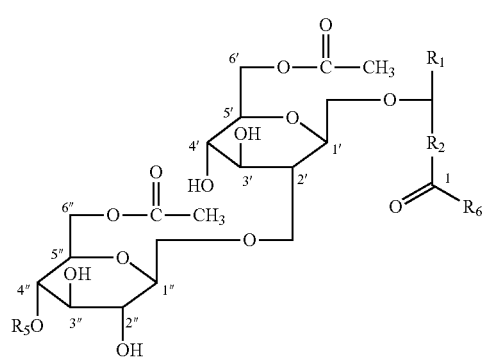

(IV)

In Formula (IV), $R_1$ represents a methyl group.

$R_2$ is a $C_{15}$ alkenylene group having one double bond, and $R_5$ represents an oleic acid residue having hydroxy. $R_6$ forms a single bond together with $R_7$ shown in Formula (V) below.

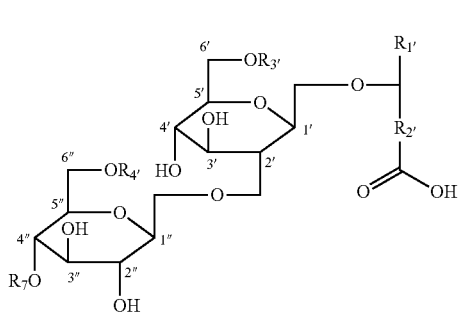

(V)

In Formula (V), $R_{1'}$ represents a methyl group.

$R_{2'}$ represents a $C_{13}$ alkylene group, $R_{3'}$ represents a hydrogen atom, and $R_{4'}$ represents an acetyl group.

(II) Method for Producing Novel SL Compound

The SL compound of the present invention may be prepared from a culture obtained from culturing yeast.

(II-1) Microorganisms

Preferable examples of yeast used for the culture include *Candida bombicola*. *Candida bombicola* is currently known as genus *Starmerella*. The yeast is a publicly known SL-producing yeast capable of SL production in significant amount (acidic SL, lactonic SL) (e.g., Canadian Journal of Chemistry, 39, 846 (1961) (note: genus *Torulopsis* disclosed in this document is classified as genus *Candida*; however, for the reason above, it is now classified as genus *Starmerella*), Applied and Environmental Microbiology, 47, 173 (1984)). In addition, *Candida* (*Starmerella*) *bombicola* is registered to the bioresource bank ATCC (American Type Culture Collection), and can be obtained from the ATCC (e.g., *Candida bombicola* ATCC22214). Further, other SL-producing *Candida* yeasts known for the production of SL (acidic SL, lactonic SL) may presumably be used for the production of the SL compound of the present invention. Examples of such SL-producing yeasts include *Candida magnoliae*, *Candida gropengisseri*, and *Candida apicola*. Production of a relatively large amount of SL in the culture solutions of these yeasts has already been reported (R. Hommel, Biodegradation, 1, 107 (1990)).

(II-2) Culture Medium and Culture Conditions

The culture of yeast in the present invention uses culture mediums containing, as carbon sources, sugars such as glucose (hydrophilic substrate), or fatty acids, fatty acid esters such as fatty acid triglyceride, and oils and fats such as vegetable oils containing fatty acid as a component (hydrophobic substrate). Other conditions of the culture medium are not particularly limited; other components of the medium may be suitably selected from medium components generally used for yeasts.

The fatty acid moiety of SL is known to depend on the chain length and the proportion of the fatty acid added as a hydrophobic substrate of a medium component. This is also the case in the SL compound of the present invention, and the chain length and the proportion of the fatty acid in the SL compound may be controlled by suitably selecting the hydrophobic substrate to be added to the medium. For example, by using a $C_{12-20}$ long-chain saturated fatty acid such as lauric acid (12:0), myristic acid (14:0), pentadecylic acid (15:0), palmitic acid (16:0), margaric acid (17:0), stearic acid (18:0), arachidic acid (20:0), or a lipid containing such saturated fatty acid at a high proportion as the hydrophobic substrate, it is possible to produce an SL compound having, as a constituent, such a saturated fatty acid residue or a chain (alkylene group) derived from the fatty acid. Further, by using a $C_{16-20}$ long-chain unsaturated fatty acid having 1 to 3 double bonds such as palmitoleic acid (16:1), oleic acid (18:1), vaccenic acid (18:1), linoleic acid (18:2), (9,12,15)-linolenic acid (18:3), (6,9,12)-linolenic acid (18:3), eleostearic acid (18:3), 8,11-eicosadienoic acid (20:2) or 5,8,11-eicosatrienoic acid (20:3), or lipids having these unsaturated fatty acids at high proportions as a hydrophobic substrate, it is possible to produce SL compounds having these unsaturated fatty acid residues or chains (alkenylene group) derived from them.

Any oil-based substrates that have been reported usable for SL production by culture may be used as hydrophobic substrates (oil-based substrate). Reported examples of hydrophobic substrates include vegetable oils and fats (Zhou et al., J. Am. Oil. Chem. Soc., 69: 89-91 (1992), etc.), animal oils and fats (Deshpande et al., Bioresource Technol., 54:

143-150 (1995)), fatty acids (Asmer et al., J. Am. Oil. Chem. Soc., 65: 1460-1466 (1988), etc.), fatty acid esters (Davila et al., Appl. Microbiol. Biotechnol., 38: 6-11 (1992)), and n-alkanes (Tulloch et al., Can. J. Chem., 46: 3337-3351 (1968). Preferable examples include vegetable oils and fats or fatty acids, and fatty acid esters produced by using vegetable oils as a raw material. Generally, edible vegetable oils are used as vegetable oils. Examples of vegetable oils include soybean oil, rapeseed oil, cottonseed oil, sunflower oil, kapok oil, sesame oil, corn oil, rice oil, peanut oil, safflower oil, olive oil, linseed oil, tung oil, castor oil, palm oil, palm kernel oil, coconut oil, and mixtures thereof. Soybean oil, rapeseed oil, sunflower oil, safflower oil, and mixtures thereof are preferable. These fatty acids have 6 to 24, preferably 12 to 20 carbon atoms, and may have 0 to 3 unsaturated bonds in each molecule. Examples of fatty acids include saturated fatty acids such as caproic acid, caprylic acid, capric acid, undecanoic acid, lauric acid, tridecanoic acid, myristic acid, pentadecanoic acid, palmitic acid, margaric acid, stearic acid, nonadecanoic acid, arachidic acid, behenic acid, or lignoceric acid; unsaturated fatty acids such as obtusilic acid, linderic acid, tsuzuic acid, myristoleic acid, palmitoleic acid, petroselinic acid, oleic acid, elaidic acid, vaccenic acid, erucic acid, linoleic acid, γ-linolenic acid, or linolenic acid; and mixtures thereof. Examples of fatty acid esters include the fatty acid esters described above. The concentration of the oil-based substrate that can be added to the beginning of the culture is in a range of 50 to 200 g/L, preferably 100 to 150 g/L. When the oil-based substrate is successively supplied, the oil-based substrate in an amount corresponding to the above concentration is supplied to the culture system at a constant speed during the culture period.

Preferable examples of hydrophobic substrate include oleic acid, which is a $C_{18}$ unsaturated fatty acid having one double bond, or a lipid containing oleic acid at a high proportion. Examples of lipids include vegetable oils such as palm oil, rice bran oil, rapeseed oil, olive oil, or safflower oil, and animal oils such as lard or beef oil. Further, by using a mixed substrate of triglyceride and oleic acid as a hydrophobic substrate, it is possible to obtain an SL compound having an oleic acid residue or a chain (alkenylene group) derived from the oleic acid at high yield.

In terms of industrial application, stable and large-amount/high-yield SL compound production by fermentation is required. To this end, it is preferable to use a mixture of a hydrophobic substrate (long-chain saturated or unsaturated fatty acid, lipid) and a hydrophilic substrate as a carbon source.

Examples of the hydrophilic substrate include monosaccharides such as glucose, fructose, or galactose; and disaccharides such as sucrose or maltose. Glucose is preferable.

In particular, a suitable culture medium composition for the production of the SL compound of the present invention using Candida [Starmerella] bombicola (ATCC22214) strain is shown below.

Yeast Extract: 1 to 6 g/L, preferably 2 to 5 g/L, more preferably 2.5 to 4.5 g/L,
Long-Chain Saturated or Unsaturated Fatty Acid: 50 to 200 g/L, preferably 50 to 170 g/L, more preferably 50 to 150 g/L,
Lipid (oils or fats): 50 to 200 g/L, preferably 50 to 170 g/L, more preferably 50 to 150 g/L,
Sugar (glucose): 50 to 200 g/L, preferably 50 to 150 g/L, more preferably 70 to 120 g/L,
Sodium Chloride: 0.1 to 5 g/L, preferably 0.1 to 3 g/L, more preferably 0.5 to 1.5 g/L,
Monopotassium Phosphate: 5 to 50 g/L, preferably 5 to 35 g/L, more preferably 10 to 25 g/L,
Magnesium Sulfate; 1 to 50 g/L, preferably 1 to 30 g/L, more preferably 5 to 15 g/L,
Peptone: 1 to 50 g/L, preferably 1 to 30 g/L, more preferably 5 to 15 g/L,
Urea: 0.01 to 10 g/L, preferably 0.01 to 5 g/L, more preferably 0.05 to 3 g/L.

The method for producing the SL compound of the present invention (culture of SL-producing yeast) is not particularly limited, and a suitable method may be selected according to the objective. However, it is preferable to increase the culture scale from the seed culture to the main culture according to the standard method. The medium and conditions used in the culture are exemplified below.

a) Seed Culture

A Candida (Starmerella) bombicola (ATCC22214) strain is subjected to shaking culture in a liquid medium containing 10 g/L of aqueous glucose, 5 g/L of yeast extract, and 10 g/L of peptone at 30° C. for two days.

b) Main Culture

The culture solution obtained by the above seed culture is inoculated as an inoculum in a liquid medium (having a pH of 4 to 5 before sterilization) containing 50 g/L of lipid (oils or fats), 50 g/L of long-chain saturated or unsaturated fatty acid, 100 g/L of aqueous glucose, 2.5 g/L of yeast extract, 1 g/L of sodium chloride, 20 g/L of monopotassium phosphate, 10 g/L of magnesium sulfate heptahydrate, and 1 g/L of urea; and is subjected to aeration culture at a temperature of about 30° C. for six days for fermentation.

As described above, suitable lipid (oils and fats) and the long-chain saturated or unsaturated fatty acid may be selected according to the fatty acid residue or fatty acid-derived group (alkylene group, alkenylene group) constituting the SL compound of the present invention. For example, when an SL compound containing, as a constituent, an oleic acid residue or oleic acid-derived group (a $C_{18}$ alkenylene group having one double bond; in Formula (I), $R_2$ is a $C_{15}$ alkenylene group having one double bond) is produced, a vegetable oil containing, as a long-chain saturated or unsaturated fatty acid, oleic acid, and containing, as a lipid (oils or fats), an oleic acid residue, such as palm oil, rice bran oil, rapeseed oil, olive oil, safflower oil, and the like are suitably used.

Further, for example, the following method may be used as a method for obtaining a fraction containing the SL compound of the present invention from the culture thus obtained above.

i) Preparation of SL-Containing Fraction (Mixture Containing Conventional SL and SL Compound of the Present Invention)

The culture obtained above was left unattended, and the generated supernatant was removed. Thereafter, water in the same amount as that of the supernatant was added. The resulting mixture was adjusted to about pH 6.5 to 7 using an alkaline component such as sodium hydroxide, thereby solubilizing SL contained in the culture. Solids were removed from the resulting mixture by centrifugation, and a supernatant with solubilized SL was collected. By adjusting the resulting mixture to pH 2 to 3 by adding, for example, a sulfuric acid aqueous solution, the SL is reinsolubilized. By collecting the insolubilized mixture, it is possible to obtain an SL-containing fraction (a mixture containing a conventional SL and the SL compound of the present invention).

The conventional SL includes the acidic SL represented by Formula (VI) below, and the lactonic SL represented by Formula (VII) below.

Acidic SL

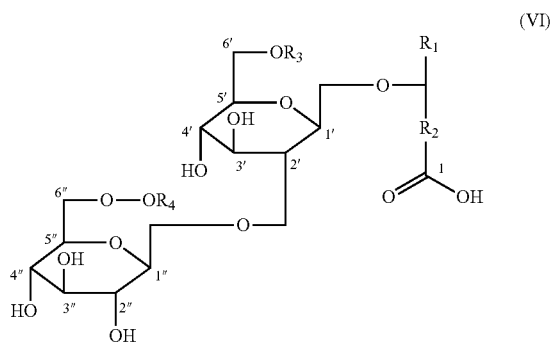

In Formula (VI), $R_1$ represents a hydrogen atom or methyl group.

$R_3$ and $R_4$ are the same or different, and each represents a hydrogen atom or acetyl group.

$R_2$ represents a $C_{9-18}$ alkylene group, or $C_{9-18}$ alkenylene group having 1 to 3 double bonds.

Lactonic SL

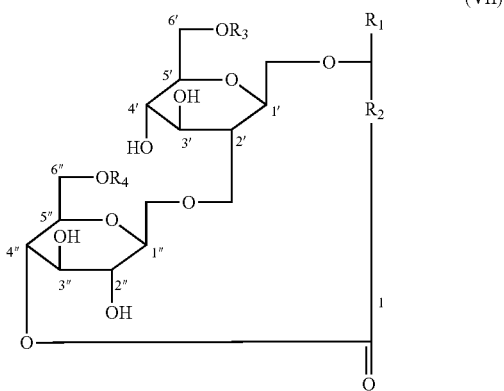

In Formula (VII), $R_1$ represents a hydrogen atom or methyl group.

$R_3$ and $R_4$ are the same or different, and each represents a hydrogen atom or acetyl group.

$R_2$ represents a $C_{9-18}$ alkylene group, or $C_{9-18}$ alkenylene group having 1 to 3 double bonds.

ii) Isolation of SL Compound of the Present Invention from SL-Containing Fraction By performing, for example, reverse-phase column chromatography using C18 ODS column, a fraction containing the SL compound of the present invention can be isolated from an SL-containing fraction containing both conventional SL (acidic SL, lactonic SL) and the SL compound of the present invention. More specifically, as shown in Example 1(2), in the reverse-phase column chromatography using a C18 ODS column as a solid phase and a 50 to 95 vol % aqueous ethanol solution as a mobile phase, the conventional SL, i.e., the acidic SL and the lactonic SL, are both eluted with a 80 vol % aqueous ethanol solution, whereas the SL compound of the present invention is eluted with an aqueous ethanol solution whose ethanol concentration is 90 vol % or more. The SL compound of the present invention is roughly classified into an SL compound (monomeric SL compound) in which $R_6$ in Formula (I) is hydroxy, and an SL compound (dimeric SL compound) in which $R_6$ forms a single bond together with $R_7$ in Formula (II) to form a dimer. The former, i.e., the "monomeric SL compound," can be eluted and isolated by reverse-phase column chromatography using an aqueous ethanol solution whose ethanol concentration is 90 vol %; and the latter, i.e., the "dimeric SL compound," can be eluted and isolated by reverse-phase column chromatography using an aqueous ethanol solution whose ethanol concentration is 95 vol %.

The fraction (X1 fraction) eluted and isolated with a 90 vol % aqueous ethanol solution contains multiple kinds of the "monomeric SL compound" in which $R_6$ in Formula (I) is hydroxy. These compounds belong to a compound group having a peak in an area of a retention time from 45 to 60 minutes in HPLC under the conditions in later-described Table 1 (see FIG. 1).

These X1 fractions include the compound (monomeric SL compound) represented by Formula (III) below, which is denoted by peak 26 (retention time=54 minutes) in the chromatogram shown in FIG. 1:

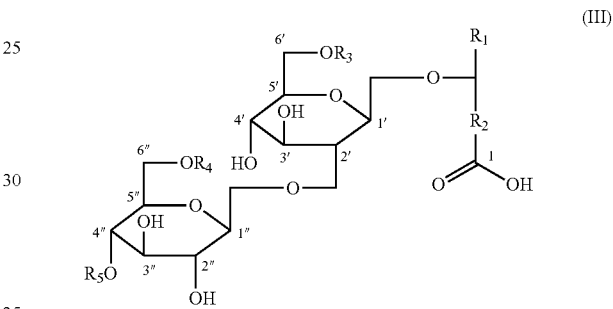

(in Formula (III), $R_1$ represents a methyl group, $R_3$ and $R_4$ are both acetyl groups, $R_2$ represents a $C_{15}$ alkenylene group, and $R_5$ represents an oleic acid residue having hydroxy.), as well as a compound in which the fatty acid residue represented by $R_5$ and/or the aliphatic residue derived from the fatty acid represented by $R_2$ in Formula (III) have a chain length different from that of the above Compound (III). More specifically, the X1 fractions include an SL compound in which $R_1$ is a methyl group, $R_3$ and $R_4$ are both acetyl groups, $R_2$ is a $C_{9-12}$ alkylene group or $C_{13-12}$ alkenylene group having 1 to 3 double bonds, and $R_5$ is a $C_{12-20}$ fatty acid residue that may have or may not have hydroxy (for convenience, this group of compounds is referred to as "monomeric SL compound example 1").

Further, the X1 fraction includes an SL compound in which $R_1$ is a hydrogen atom, instead of a methyl group as in the above compound (monomeric SL compound example 1); an SL compound in which $R_3$ and $R_4$ are hydrogen atoms, instead of acetyl groups as in the above compound; an SL compound in which one of $R_3$ and $R_4$ is a hydrogen atom while the other is an acetyl group, instead of both being acetyl groups as in the above compound; an SL compound in which $R_1$ is a hydrogen atom instead of a methyl group, and $R_3$ and $R_4$ are hydrogen atoms instead of both being acetyl groups as in the above compound; and an SL compound in which $R_1$ is a hydrogen atom instead of a methyl group, and one of $R_3$ and $R_4$ is a hydrogen atom while the other is an acetyl group instead of both being acetyl groups as in the above compound (for convenience, this group of compounds is referred to as "monomeric SL compound example 2").

Additionally, the X1 fraction includes an SL compound in which the —OR$_5$ group is bonded either at the 3', 4', 2" or 3"-position of the sophorose ring instead of being bonded at the 4"-position of the sophorose ring as in various compounds belonging to the above compound group (monomeric SL compound examples 1 and 2).

The fraction (X2 fraction) eluted and isolated with a 95 vol % aqueous ethanol solution contains multiple kinds of the "dimeric SL compound" in which R$_6$ in Formula (I) forms a single bond together with R$_7$ in Formula (II) to form a dimer. These compounds belong to a compound group having a peak in an area of a retention time from 60 to 70 minutes in HPLC under the conditions in later-described Table 1 (see FIG. 1).

These X2 fractions include the compound represented by Formula (IV) below, which is denoted by peak 36 (retention time=64 minutes) in the chromatogram shown in FIG. 1.

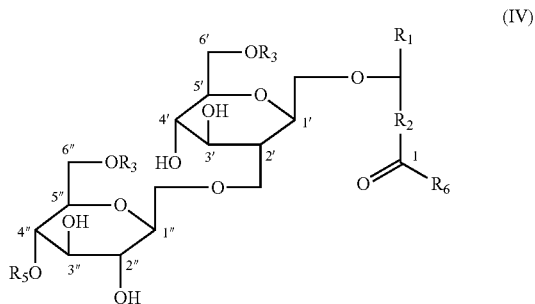

(IV)

In Formula (IV), R$_1$ is a methyl group, R$_3$ and R$_4$ are acetyl groups, R$_2$ is a C$_{15}$ alkenylene group, and R$_5$ is an oleic acid residue having hydroxy. R$_6$ forms a single bond together with R$_7$ in the group represented by Formula (V) below.

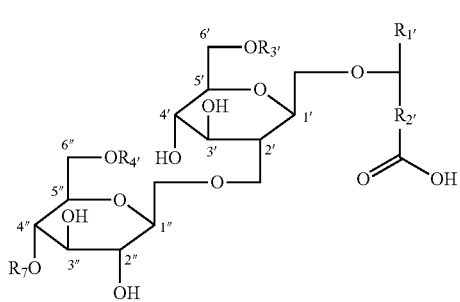

(V)

In Formula (V), R$_{1'}$ is a methyl group, R$_{3'}$ is a hydrogen atom, R$_{4'}$ is an acetyl group, and R$_{2'}$ is a C$_{13}$ alkylene group.

These X2 fractions also include a compound in which the fatty acid residue represented by R$_5$, the aliphatic residue derived from the fatty acid represented by R$_2$, and/or the aliphatic residue derived from the fatty acid represented by R$_{2'}$ in Formulas (IV) and (V) have a chain length different from that of the above Compound. More specifically, the X1 fractions include an SL compound in which R$_1$ and R$_{1'}$ are methyl groups, R$_3$ and R$_4$, R$_{3'}$ and R$_{4'}$ are all acetyl groups, R$_2$ and R$_{2'}$ are C$_{9-17}$ alkylene group or C$_{13}$-C$_{17}$ alkenylene group having 1 to 3 double bonds, and R$_5$ is a C$_{12-20}$ fatty acid residue that may have or may not have hydroxy (for convenience, this group of compounds is referred to as "dimeric SL compound example 1").

Further, the X2 fraction includes, for example, an SL compound in which R$_1$ is a hydrogen atom instead of a methyl group as in the above compound; an SL compound in which R$_3$ and R$_4$ are hydrogen atoms instead of acetyl groups as in the above compound; an SL compound in which one of R$_3$ and R$_4$ is a hydrogen atom while the other is an acetyl group instead of both being acetyl groups as in the above compound; an SL compound in which R$_1$ is a hydrogen atom instead of a methyl group, and R$_3$ and R$_4$ are hydrogen atoms instead of both being acetyl groups as in the above compound; and an SL compound in which R$_1$ is a hydrogen atom instead of a methyl group, and one of R$_3$ and R$_4$ is a hydrogen atom while the other is an acetyl group while both being acetyl groups as in the above compound (for convenience, this group of compounds is referred to as "dimeric SL compound example 2").

Further, the X2 fraction includes, for example, a compound in which R$_{1'}$ is a hydrogen atom instead of a methyl group in the various compounds belonging to the above compound groups (dimeric SL compound examples 1 and 2); a compound in which R$_{3'}$ is an acetyl group instead of a hydrogen atom as in the above compounds; a compound in which R$_{3'}$ is a hydrogen atom instead of an acetyl group as in the above compounds; a compound in which R$_1$ is a hydrogen atom instead of a methyl group, and R$_{3'}$ is an acetyl group instead of a hydrogen atom as in the above compounds; and a compound in which R$_1$ is a hydrogen atom instead of a methyl group, and R$_{4'}$ is a hydrogen atom instead of an acetyl group as in the above compounds (for convenience, this group of compounds is referred to as "dimeric SL compound example 3").

Further, the X2 fraction includes an SL compound in which the —OR$_5$ group is bonded at either the 3', 4', 2" or 3"-position of the sophorose ring, instead of at the 4"-position of the sophorose ring, as in various compounds belonging to the above compound groups (dimeric SL compound examples 1 to 3); and an SL compound in which the —OR$_7$ group is bonded at either the 3', 4', 2" or 3"-position of the sophorose ring, instead of at the 4"-position of the sophorose ring as in Formula (V).

As shown in the Test Examples described later, the SL compounds, including both the monomeric SL compound and the dimeric SL compound, of the present invention have distinct characteristics including surfactant performance, in particular, surface tension and emulsifying capacity, and also have no or greatly attenuated bitterness unlike the conventional acidic SL and lactonic SL.

(III) Composition Containing Novel Sophorolipid Compound

The composition of the present invention is characterized by comprising the SL compound of the present invention represented by Formula (I). However, the composition does not include natural products, or cultures of a raw material, i.e., an SL-producing yeast. "SL compound" is a general name for the monomeric SL compounds and the dimeric SL compounds described above. The compositions of the present invention include a composition that comprises only a monomeric SL compound as an SL compound, a composition that comprises only a dimeric SL compound as an SL compound, and a composition that comprises both a monomeric SL compound and a dimeric SL compound.

The composition of the present invention is characterized by having surfactant performance, in particular, surface tension and emulsifying capacity, based on the characteristics of the above SL compound (I) of the present invention.

Preferably, the composition of the present invention includes at least the monomeric SL compound represented by Formula (III), and/or the dimeric SL compound represented by Formula (IV), and has surfactant performance, in particular, surface tension and emulsifying capacity.

The composition of the present invention may be used as a surfactant for food or beverages, cosmetics, pharmaceuticals, quasi-drugs, and additives thereof (for example, emulsifier, antifoaming agent, coagulant, preservative, binder, stabilizer, etc.) based on the surfactant performance of the SL compound of the present invention. In particular, as mentioned above, since the SL compound of the present invention has no or greatly attenuated bitterness, the composition of the present invention may be applied to products that are to be used in the oral cavity, to be orally administered, or to be possibly entered into mouths, such as food or beverages, cosmetics, oral pharmaceuticals, or quasi-drugs.

Examples of the cosmetics that may be entered into mouths include lotions, emulsions, creams, lipsticks, lip balms, facial wash, facial cleansing, shampoo, and conditioner. Further, examples of the products that are used in the oral cavity include, in addition to food or beverages and pharmaceuticals, mouth wash, toothpastes, and mouth deodorants.

The proportion of the SL compound in the composition of the present invention is not particularly limited and may be appropriately set according to the need, insofar as the surfactant performance, in particular, surface tension and emulsifying capacity, of the composition of the present invention can be ensured. For example, the total amount of the SL compound is selected from a range of 0.01 to 100 wt %, preferably a range of 0.05 to 30 wt %, according to the usage of the composition.

EXAMPLES

The structures and the effects of the present invention are more specifically described below with reference to Examples and Test Examples. However, the present invention is not limited to the Test Examples.

Example 1: Preparation and Identification of Novel Sophorolipid (X1 and X2)

(1) Preparation of Mixture Containing Conventional SL and Novel SL (Conventional SL/Novel SL-Containing Mixture)

A liquid medium containing, per liter, 10 g of aqueous glucose (produced by Nihon Shokuhin Kako Co., Ltd., product name: Nisshoku Gansui Kessho Budoto), 10 g of peptone (produced by Oriental Yeast Co., Ltd., product name: Peptone CB90M), and 5 g of a yeast extract (produced by Asahi Food & Healthcare Co., Ltd., product name: Meast Powder N) was used as a culture medium. *Candida bombicola* ATCC 22214 was cultured in the medium while shaking at 30° C. for two days. This was used as a pre-culture fluid.

The pre-culture fluid was inoculated in a proportion of 4 mass % into a main culture medium (3 L) placed in a 5-liter fermenter, and then cultured at 30° C. at an aeration rate of 0.6 vvm for 6 days for fermentation. The main culture medium contained, per liter, 100 g of aqueous glucose, 50 g of palm olein (produced by NOF Corporation, product name: Palmary 2000), 50 g of oleic acid (produced by Acid Chem, product name: Palmac 760), 1 g of sodium chloride, 10 g of monopotassium phosphate, 10 g of magnesium sulfate heptahydrate, 2.5 g of yeast extract (produced by Asahi Food & Healthcare Co., Ltd., product name: Meast Powder N), and 1 g of urea (pH 4.5 to 4.8 before sterilization).

On the 6th day from the start of culturing, the fermentation was stopped. The culture fluid removed from the fermenter was heated to 50 to 80° C., then returned to room temperature, and allowed to stand for 2 to 3 days. As a result, the culture was separated into the following three layers in this order from the bottom: a liquid brown precipitate layer; a milky-white solid layer presumably mainly containing fungal cells; and a supernatant. After the supernatant was removed, industrial water or groundwater was added in an amount equal to the amount of the supernatant removed. While the resulting mixture was stirred, a 48 mass % aqueous sodium hydroxide solution was gradually added to achieve a pH of 6.5 to 6.9, and SL contained in the culture fluid was solubilized. The resulting product was centrifuged (2,400×g, 15 minutes, room temperature (25° C.)) by a tabletop centrifuge (Westfalia: produced by Westfalia separator AG) to precipitate milky-white solids, and the supernatant was collected. While the collected supernatant was stirred, an aqueous sulfuric acid solution having a concentration of 62.5 mass % was gradually added to achieve a pH of 2.5 to 3.0, and the SL was insolubilized again. After this was allowed to stand for two days, the supernatant was removed by decantation as much as possible, thus obtaining the residue (about 50% water content). As described later, the residue was a mixture containing both conventional SL and the novel SL. This mixture is referred to as a "conventional SL/novel SL-containing mixture."

As described later, the "conventional SL/novel SL-containing mixture" contains 60 mass % of conventional SL and 40 mass % of the novel SL, based on the total SL amount (100 mass %).

(2) Separation of Conventional SL from Novel SL

The 600 g (about 50% water content) of the "conventional SL/novel SL-containing mixture" obtained above was subjected to reverse-phase column chromatography under the following conditions.

Solid phase: C18 column (COSMOSIL 40C18-PREP, produced by Nacalai Tesque, Inc., 7.5 kg)

Mobile phase: Aqueous ethanol solution having an ethanol concentration of 50 to 95 vol %.

More specifically, a solution obtained by mixing 600 g of 50% aqueous ethanol solution with 600 g (about 50% water content) of the "conventional SL/novel SL-containing mixture" was added to the C18 column (7.5 kg), and 10 L of 50% aqueous ethanol solution and then 10 L of 80% aqueous ethanol solution were subsequently added thereto, thereby eluting the conventional SL (acidic SL, lactonic SL). Subsequently, 15 L of 90% aqueous ethanol solution was supplied to elute and isolate a novel SL (X1). Then, 15 L of 95% aqueous ethanol solution was supplied to elute and isolate a novel SL (X2).

(3) Confirmation of Novel SL (X1) and Novel SL (X2)

A fraction eluted with a 50% aqueous ethanol solution, a fraction eluted with a 80% aqueous ethanol solution, a fraction eluted with a 90% aqueous ethanol solution, and a fraction eluted with a 95% aqueous ethanol solution obtained in the above column chromatography were subjected to high-performance liquid chromatography (HPLC) under the conditions specified in the table below, and the elution behaviors of the substances contained in each elution fraction were confirmed. More specifically, each elution fraction was evaporated and dried to hardness, and then was dissolved in ethanol. With these test samples, HPLC was performed under the following conditions.

TABLE 1

| Analysis Conditions | |
| --- | --- |
| Device | LC-10AD-VP (Shimazdu Co.) |
| Column | Inertsil ODS-3 (4.6 mm × 250 mm) |
| Temperature of Column | 40° C. |
| Mobile Phase | (A) Distilled water, (B) Methanol containing 0.1% formic acid [Gradient] 0 min → 60 min: (B) 70% → 100% 60 min → 70 min: (B) 100% → 70% |
| Flow Rate | 1.0 mL/min |
| Sample Preparation | Ethanol |
| Amount Supplied | 10 μL |
| Detector | Evaporative Light Scattering Detector (ELSD-LT II produced by Shimazdu Co.) |
| Temperature of Detector | 40° C. |
| Gain | 5 |
| Gas Pressure | 350 kPa ($N_2$ Gas) |

As a result, it was confirmed that the fraction eluted with a 80% aqueous ethanol solution contained a conventional SL (acidic SL, lactonic SL), and that neither the fraction eluted with a 90% aqueous ethanol solution (hereinafter may also be referred to as "X1 fraction") nor the fraction eluted with a 95% aqueous ethanol solution (hereinafter may also be referred to as "X2 fraction") contained a conventional SL (acidic SL, lactonic SL), by comparison with the retention time of a standard product of a conventional SL (acidic SL, lactonic SL). In the HPLC under the above conditions, among the conventional SL, the acidic SL was eluted in an area of a retention time of 10 to 25 minutes, and the lactonic SL was eluted in an area of a retention time of 25 to 40 minutes. In contrast, it was confirmed that the fraction eluted with a 90% aqueous ethanol solution (X1 fraction) contained a substance having a peak in an area of a retention time of 45 to 60 minutes, and the fraction eluted with a 95% aqueous ethanol solution (X2 fraction) contained a substance having a peak in an area of a retention time of 60 to 70 minutes, in the HPLC under the above conditions.

In order to compare the elution behaviors of the conventional SL (acidic SL, lactonic SL), the X1 fraction, and the X2 fraction to each other, a mixture of a fraction eluted with a 80% aqueous ethanol solution (containing conventional SL (acidic SL, lactonic SL)), a fraction eluted with a 90% aqueous ethanol solution (X1 fraction) and a fraction eluted with a 95% aqueous ethanol solution (X2 fraction) was subjected to HPLC under the above conditions. FIG. 1 shows the results (chromatogram).

The results showed that the substances contained in the fraction eluted with a 90% aqueous ethanol solution and the fraction eluted with a 95% aqueous ethanol solution were different from the conventional SL (acidic SL, lactonic SL) eluted with a 80% aqueous ethanol solution, and that the substances were compounds more hydrophobic than the conventional SL.

The HPLC analysis (peak area ratio) also revealed that the "conventional SL/novel SL-containing mixture" obtained in (1) contained 17.5 mass % of an acidic conventional SL, 42.5 mass % of a lactonic conventional SL, 19.5 mass % of a novel SL (X1), and 20.5 mass % of a novel SL (X2), based on the total SL amount (100 mass %).

(4) Identification of Novel SL (X1 and X2)

The structures of the compound contained in the fraction eluted with a 90% aqueous ethanol solution (X1 fraction) and the compound contained in the fraction eluted with a 95% aqueous ethanol solution (X2 fraction) were determined as follows.

(4-1) FTIR

Figure 2:
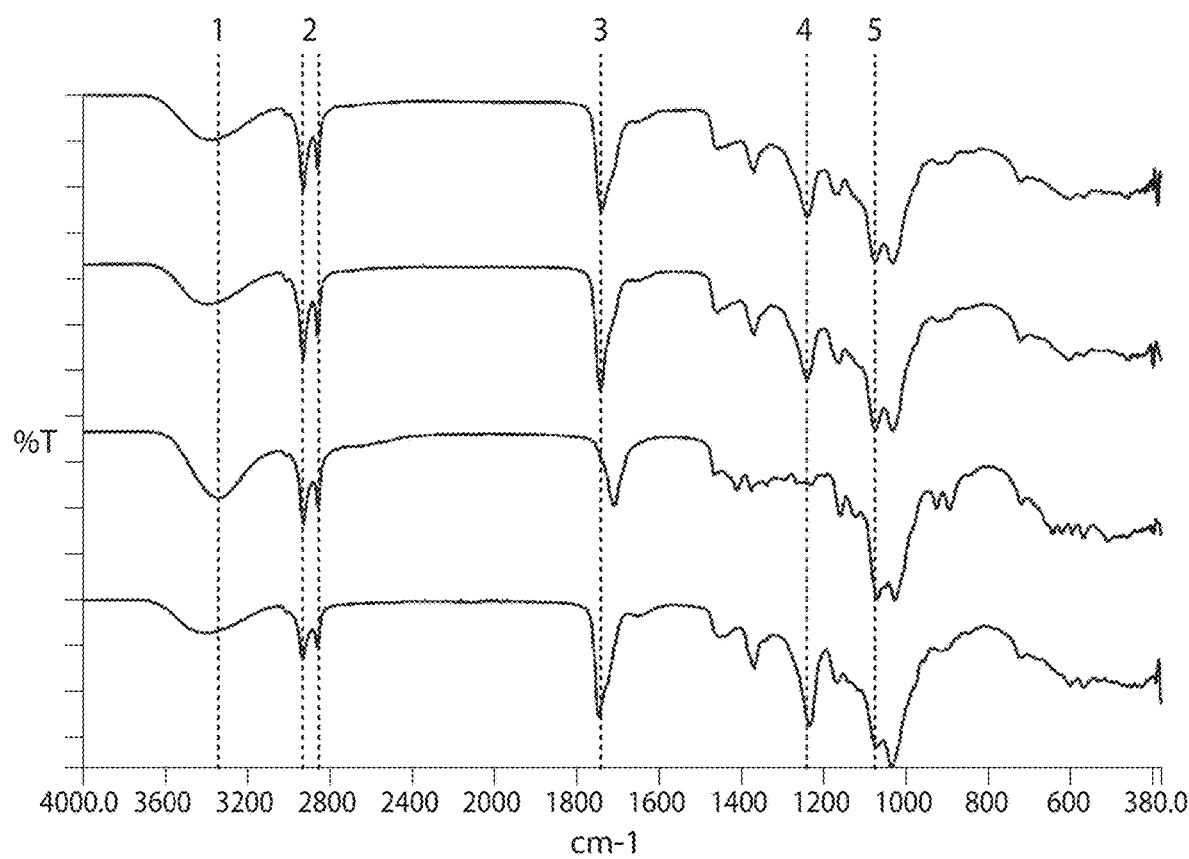
FIG. 2 shows infrared absorption spectra of an X1 fraction, an X2 fraction, an acidic SL (without acetyl group), and a lactonic SL (having two acetyl groups) in this order from the top (see Example 1(4)(4-1) FTIR).

The X1 fraction and the X2 fraction were freeze-dried to prepare test samples. Infrared absorption spectra were analyzed by the ATR method using a Spectrum TM100 (PerkinElmer Co., Ltd.) Fourier transform infrared spectrometer. FIG. 2 shows the obtained infrared absorption spectra, together with the analysis results of the conventional SL (acidic SL, lactonic SL). The acidic SL used herein is a compound in which $R_3$ and $R_4$ in Formula (VI) are both hydrogen atoms, and the lactonic SL used herein is a compound in which $R_3$ and $R_3$ in Formula (VII) are both acetyl groups.

FIG. 2 shows infrared absorption spectra of the X1 fraction, the X2 fraction, the acidic SL, and the lactonic SL, in this order from top to bottom. As shown in FIG. 2, peaks were detected at 3340 $cm^{-1}$ (Reference Number 1: OH stretching), 2920 $cm^{-1}$, 2850 $cm^{-1}$ (Reference Number 2: —$CH_2$, derived from methylene chain), 1740 $cm^{-1}$ (Reference Number 3: C=O, derived from carboxylic acid), 1240 $cm^{-1}$ (Reference Number 4: C=O, acetyl-derived carbonyl), and 1040 $cm^{-1}$ (Reference Number 5: C—O—H, derived from sugar). The results enabled the prediction that the compounds contained in the X1 fraction and the X2 fraction have an SL-like structure similar to the structure of conventional SL.

(4-2) Gas Chromatography (GC)

12.1 mL of a mixture of methanol and hydrochloric acid (mixture of methanol (10.4 mL) and concentrated hydrochloric acid (1.7 mL)) was added to a mixture (114.9 mg) of the X1 fraction and the X2 fraction, and the resulting mixture was heated at 80° C. for three hours under reflux. After the mixture was cooled to room temperature, water (20 mL) and chloroform/methanol (2:1, volume ratio) (20 mL) were added. After sufficient mixing, the mixture was centrifuged, and the organic layer was isolated. The remaining aqueous layer was extracted again with chloroform/methanol (2:1, volume ratio) (20 mL), and the organic layer was isolated. The organic layer thus obtained was mixed with the organic layer previously obtained. The remaining aqueous layer was further extracted again with hexane/ethyl acetate (1:1, volume ratio) (20 mL), and the organic layer was isolated. The organic layer thus obtained was mixed with the organic layers previously obtained.

The organic layer thus collected was treated with an evaporator so as to remove the organic solvent, thereby collecting the residue (lipid). 0.5 mL of a mixture (toluene:hexane:methanol=4:1:1, volume ratio) and 20 mL trimethylsilyldiazomethane (2 M diethylether solution) were mixed with the isolated lipid (8 μl). After the mixture was reacted for 10 minutes at room temperature, the mixture was subjected to GC under the following conditions.

GC Conditions

Device: Agilent Technologies 6890N
Column: DB-23 (0.25 mm×30 m, Agilent Technologies)
Detector: FID (245° C.)
Inlet temperature: 250° C.
Elevated temperature conditions: 150° C., 0.5 min
150° C.-170° C., 4° C./min
170° C.-195° C., 5° C./min
195° C.-215° C., 10° C./min
215° C., 11 min
Split ratio: 50:1

Table 2 shows the fatty acid composition of the compound contained in the mixture of the X1 fraction and the X2 fraction calculated according to the results of GC. In the "Fatty Acid Composition" column in Table 2, the number before ":" is the number of carbon atoms in the fatty acid, and the number after ":" is the number of double bonds. Further, in Table 2, "17OH" means that $R_1$ in Formula (I) is a methyl group, and "18OH" means that $R_1$ in Formula (I) is a hydrogen atom.

TABLE 2

| Fatty Acid Composition | Mass(%) |
|---|---|
| 12:0 | 0.4 |
| 14:0 | 0.4 |
| 16:0 | 1.8 |
| 18:0 | 1.0 |
| 18:1 | 7.2 |
| 18:2 | 2.8 |
| 16:0(17OH) | 11.8 |
| 16:0(18OH) | 11.3 |
| 18:0(17OH) | 7.8 |
| 18:1(17OH) | 44.5 |
| 18:2(17OH) | 1.9 |
| 18:1(18OH) | 5.7 |
| 20:0(17OH) | 3.4 |

With these results, it was confirmed that the mixture of the X1 fraction and the X2 fraction contained a compound containing a $C_{12-20}$ saturated fatty acid residue (for example, a residue of lauric acid, myristic acid, palmitic acid, stearic acid, or arachidic acid), and a $C_{18}$ unsaturated fatty acid residue having 1 or 2 unsaturated group (for example, an oleic acid residue or linoleic acid residue). It was revealed, in particular, that the mixture contained a compound having a $C_{18}$ unsaturated fatty acid residue having one unsaturated group (oleic acid residue) (in Formula (I), $R_1$ is a methyl group) at a high proportion.

(4-3) Various NMR ($^{13}$C-NMR and $^1$H-NMR)

The peak 26 (retention time=54 minutes) and the peak 36 (retention time=64 minutes), which were the greatest peaks in the X1 fraction and the X2 fraction, respectively, were separated from the X1 fraction and the X2 fraction (the former is referred to as "novel SL (X1-26)," and the latter is referred to as "novel SL (X2-36)"). These novel SL were subjected to $^1$H-NMR and $^{13}$C-NMR analyses using a NMR device (JNM EX-270 (JEOL Ltd.)). CD$_3$OD was used as a solvent.

Figure 3A:
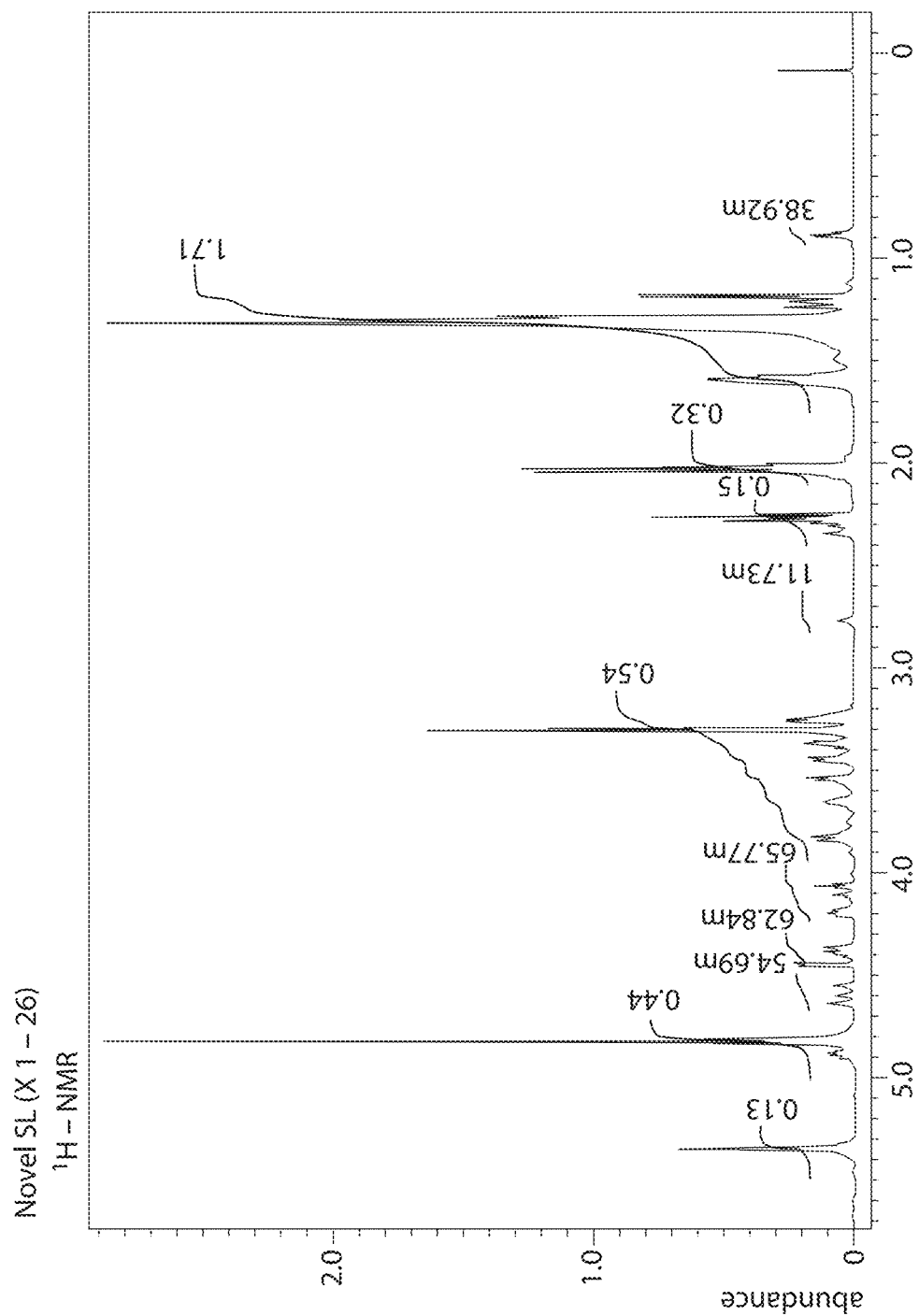
FIGS. 3A-3B show the results of (FIG. 3A) $^1$H-NMR and (FIG. 3B) $^{13}$C-NMR of a novel SL (X1-26) (the compound having peak 26 in the chromatogram of FIG. 1; the same hereinafter.).
Figure 3B:
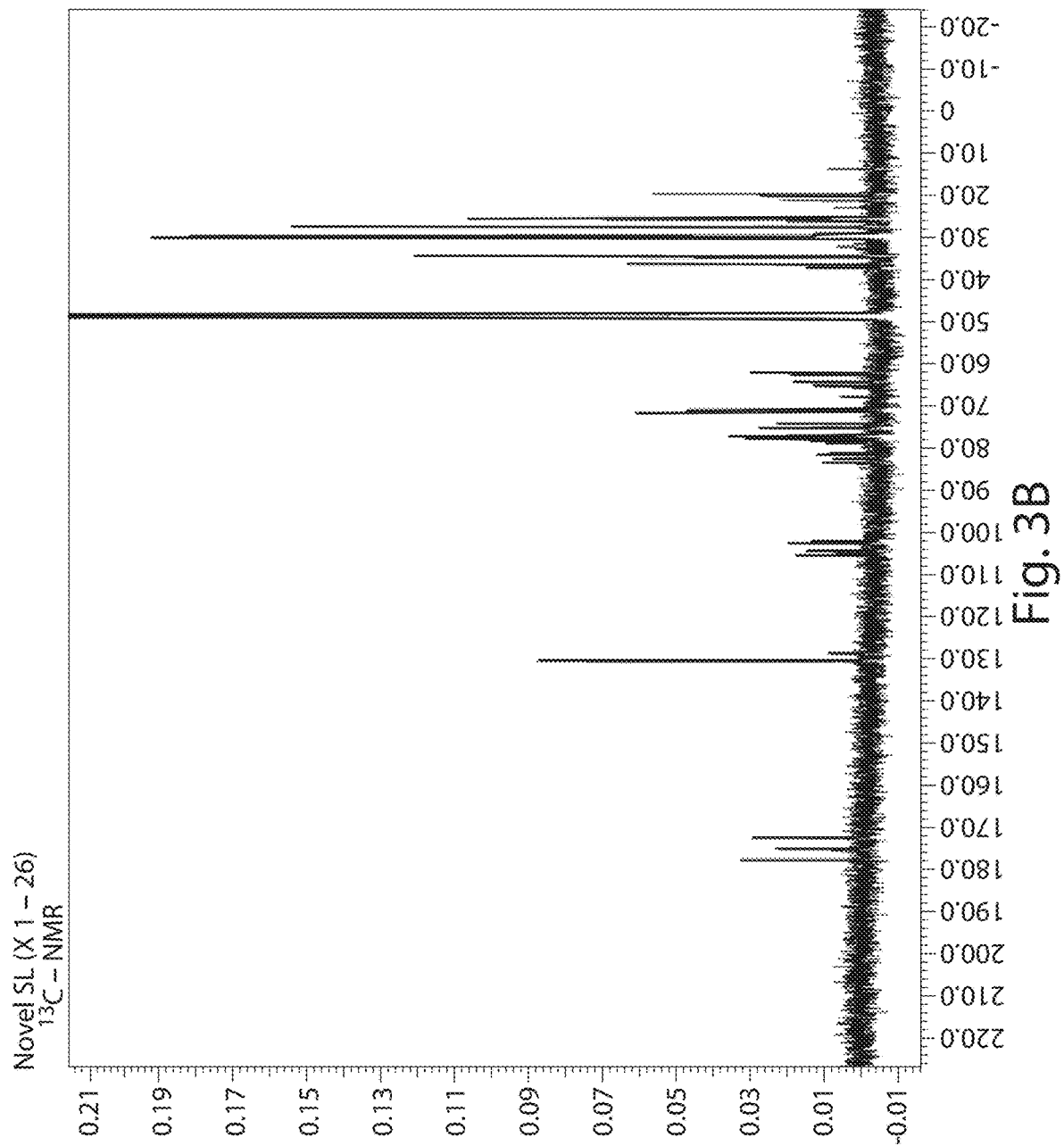
Figure 4A:
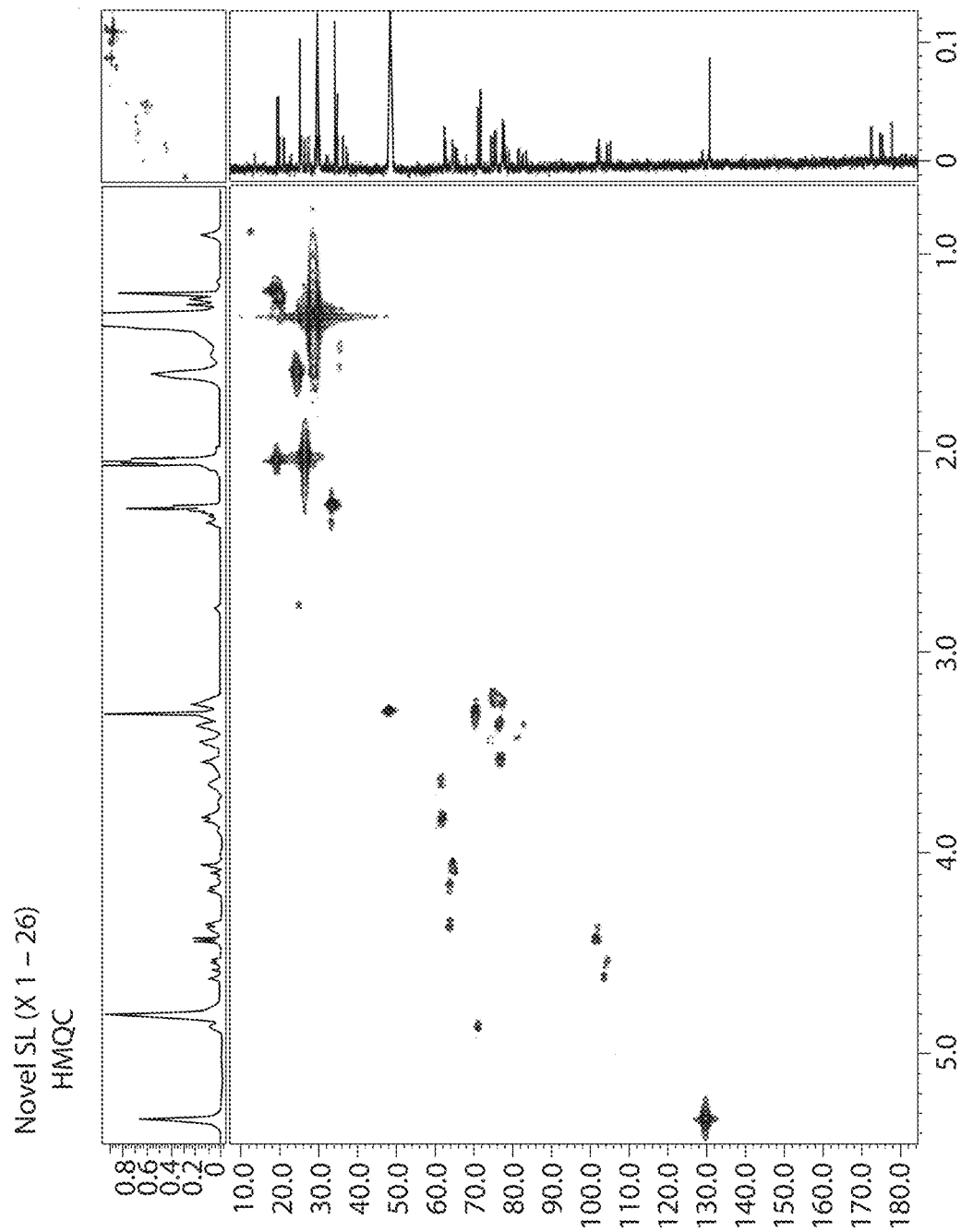
FIGS. 4A-4B show the results of (FIG. 4A) HMQC and (FIG. 4B) HMBC of the novel SL (X1-26).
Figure 4B:
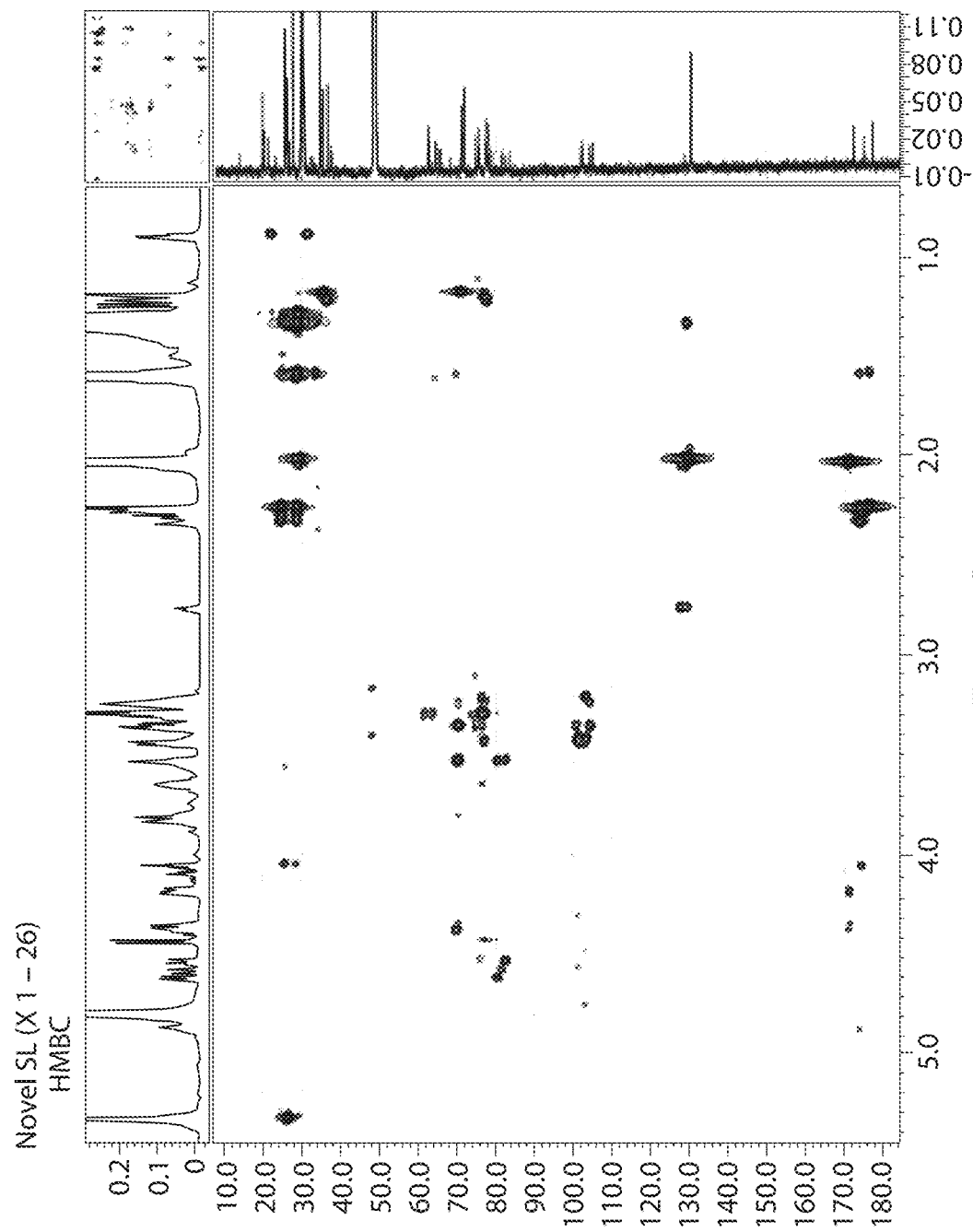
Figure 5A:
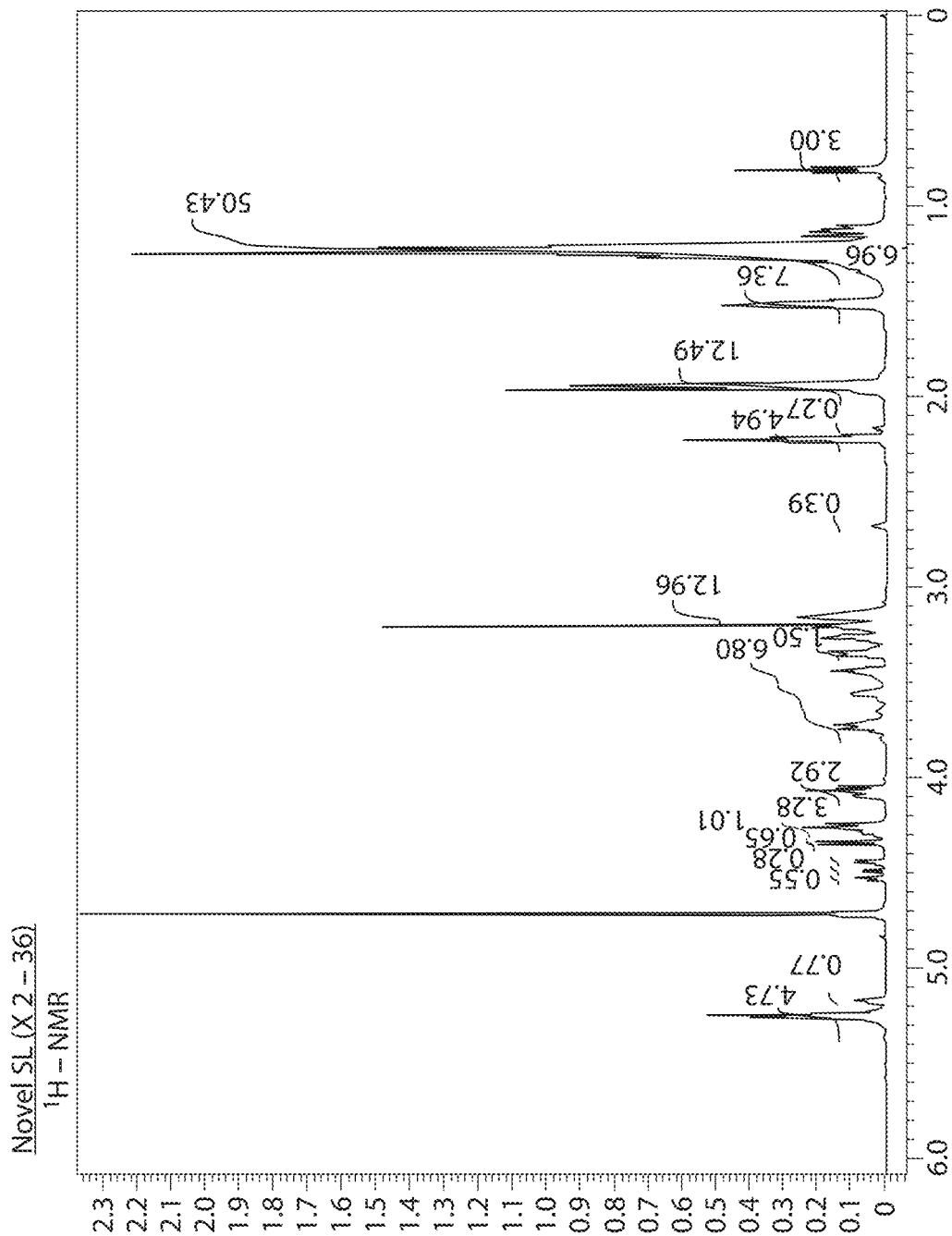
FIGS. 5A-5B show the results of (FIG. 5A) $^1$H-NMR and (FIG. 5B) $^{13}$C-NMR of a novel SL (X2-36) (the compound having peak 36 in the chromatogram of FIG. 1; the same hereinafter).
Figure 5B:
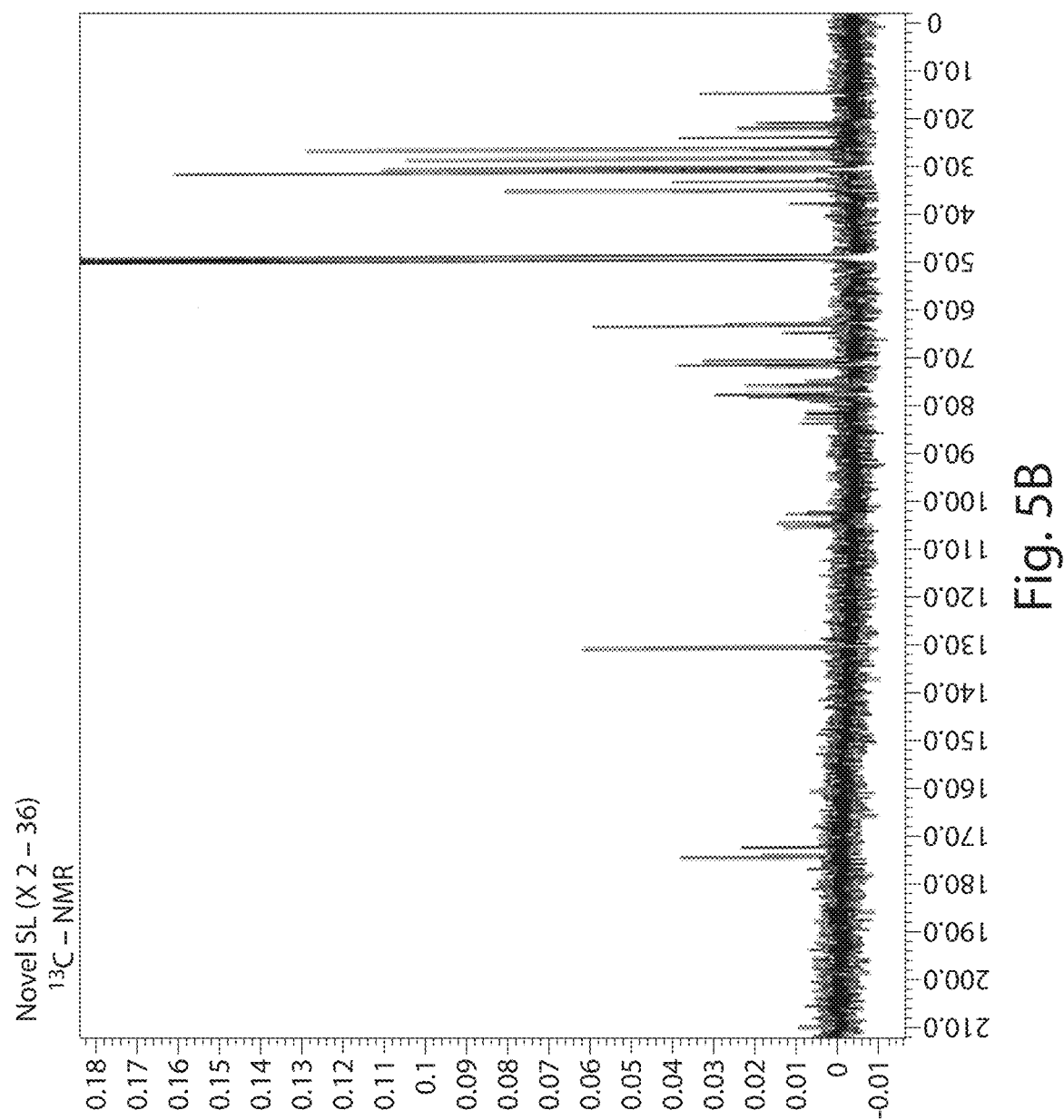
Figure 6A:
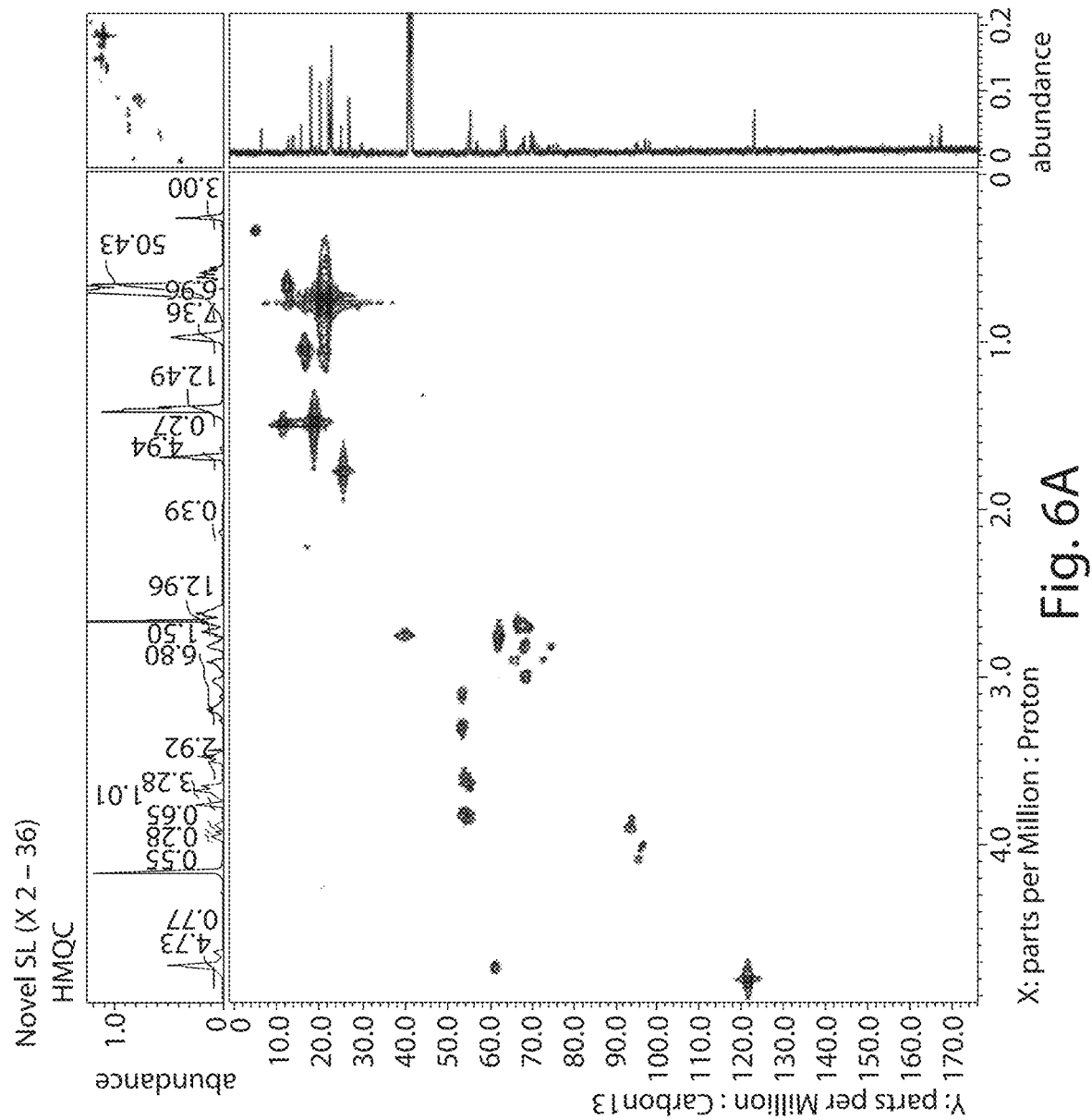
FIGS. 6A-6B show the results of (FIG. 6A) HMQC and (FIG. 6B) HMBC of the novel SL (X2-36).
Figure 6B:
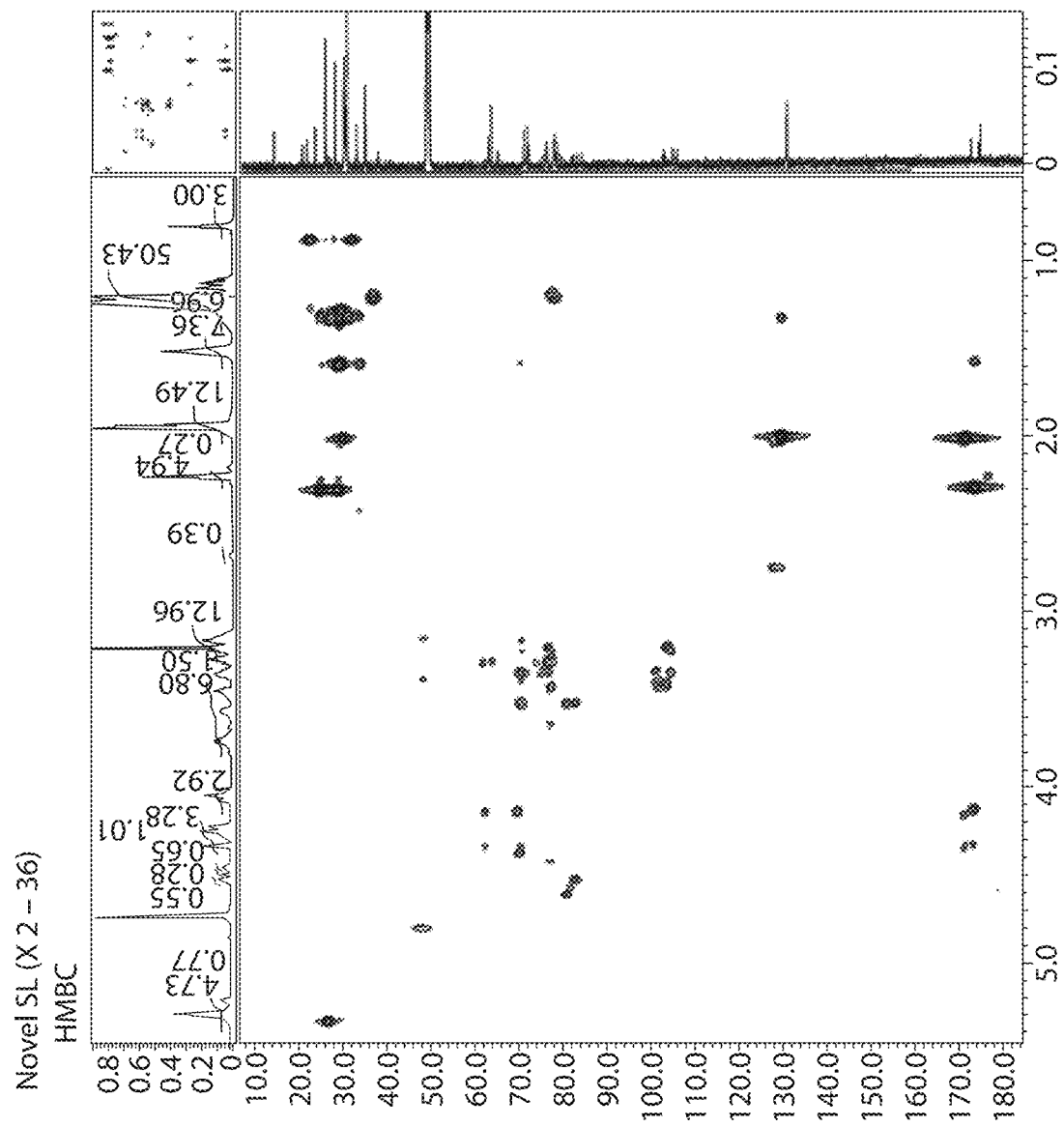

FIGS. 3A-3B show the results of $^1$H-NMR and $^{13}$C-NMR with respect to the novel SL (X1-26), and FIGS. 5A-5B show the results of $^1$H-NMR and $^{13}$C-NMR with respect to the novel SL (X2-36). FIGS. 4A-4B show a two-dimensional NMR spectrum (FIG. 4A: HMQC, FIG. 4B: HMBC) of the novel SL (X1-26), and FIGS. 6A-6B show a two-dimensional NMR spectrum (FIG. 6A: HMQC, FIG. 6B: HMBC) of the novel SL (X2-36).

The results are summarized in Tables 3 and 4.

TABLE 3

| | Novel SL (X1-26) | |
|---|---|---|
| | $^{13}$C-NMR | $^1$H-NMR |
| Sophorose | | |
| C-1' | 102.4 | 4.4 |
| C-2' | 82.7 | 3.1 |
| C-3' | 71.2 | 3.2 |
| C-4' | 70.9 | 3.4 |
| C-5' | 77.8 | 3.3 |
| C-6' | 62.7 | 4.1 |
| C-1" | 104.7 | 4.5 |
| C-2" | 74.9 | 3.3 |
| C-3" | 77.4 | 3.4 |
| C-4" | 71.4 | 4.8 |

TABLE 3-continued

| | Novel SL (X1-26) | |
|---|---|---|
| | $^{13}$C-NMR | $^1$H-NMR |
| C-5" | 77.6 | 3.5 |
| C-6" | 64.8 | 4.3 |
| Acetyl Group | | |
| —C=O(C-6', 6") | 172.4 | — |
| —CH3(C-6', 6") | 20.4, 20.7 | 1.2 |
| Acyl Group | | |
| —C=O(C-1) | 175.2, 177.5 | — |
| —CO—CH2(C-2) | 35.6 | 2.2 |
| —CO—CH2CH2(C-3) | 23.7 | 1.5 |
| —(CH2)n- | 23.6-30.8 | 1.2-1.4 |
| —CH=CH—CH2 | 28.1 | 1.9 |
| —CH=CH | 130.8, 130.9 | 5.2 |
| —OCH(CH3)—CH2(C-16) | 37.8 | 1.5 |
| —OCH(CH3)(C-17) | 78.3 | 3.6 |
| —CH3(C-18) | 21.8 | 1.1 |

TABLE 4

| | Novel SL (X2-36) | |
|---|---|---|
| | $^{13}$C-NMR | $^1$H-NMR |
| Sophorose | | |
| C-1' | 102.6 | 4.4 |
| C-2' | 82.7 | 3.1 |
| C-3' | 71.2 | 3.2 |
| C-4' | 70.8 | 3.4 |
| C-5' | 77.7 | 3.3 |
| C-6' | 62.6 | 4.1 |
| C-1" | 104.7 | 4.5 |
| C-2" | 74.9 | 3.3 |
| C-3" | 77.4 | 3.4 |
| C-4" | 71.2 | 4.8 |
| C-5" | 77.6 | 3.5 |
| C-6" | 63.2 | 4.3 |
| Acetyl Group | | |
| —C=O(C-6', 6") | 172.6 | — |
| —CH3(C-6', 6") | 20.8, 21.0 | 1.2 |
| Acyl Group | | |
| —C=O(C-1) | 174.3, 174.7 | — |
| —CO—CH2(C-2) | 34.7 | 2.2 |
| —CO—CH2CH2(C-3) | 23.7 | 1.5 |
| —(CH2)n- | 23.6-30.8 | 1.2-1.4 |
| —CH=CH—CH2 | 26.1 | 1.9 |
| —CH=CH | 130.8, 130.9 | 5.2 |
| —OCH(CH3)—CH2(C-16) | 37.8 | 1.5 |
| —OCH(CH3)(C-17) | 75.8 | 3.6 |
| —CH3(C-18) | 21.7 | 1.1 |

(4-4) DEPT135, HMQC, and HMBC

Figure 7A:
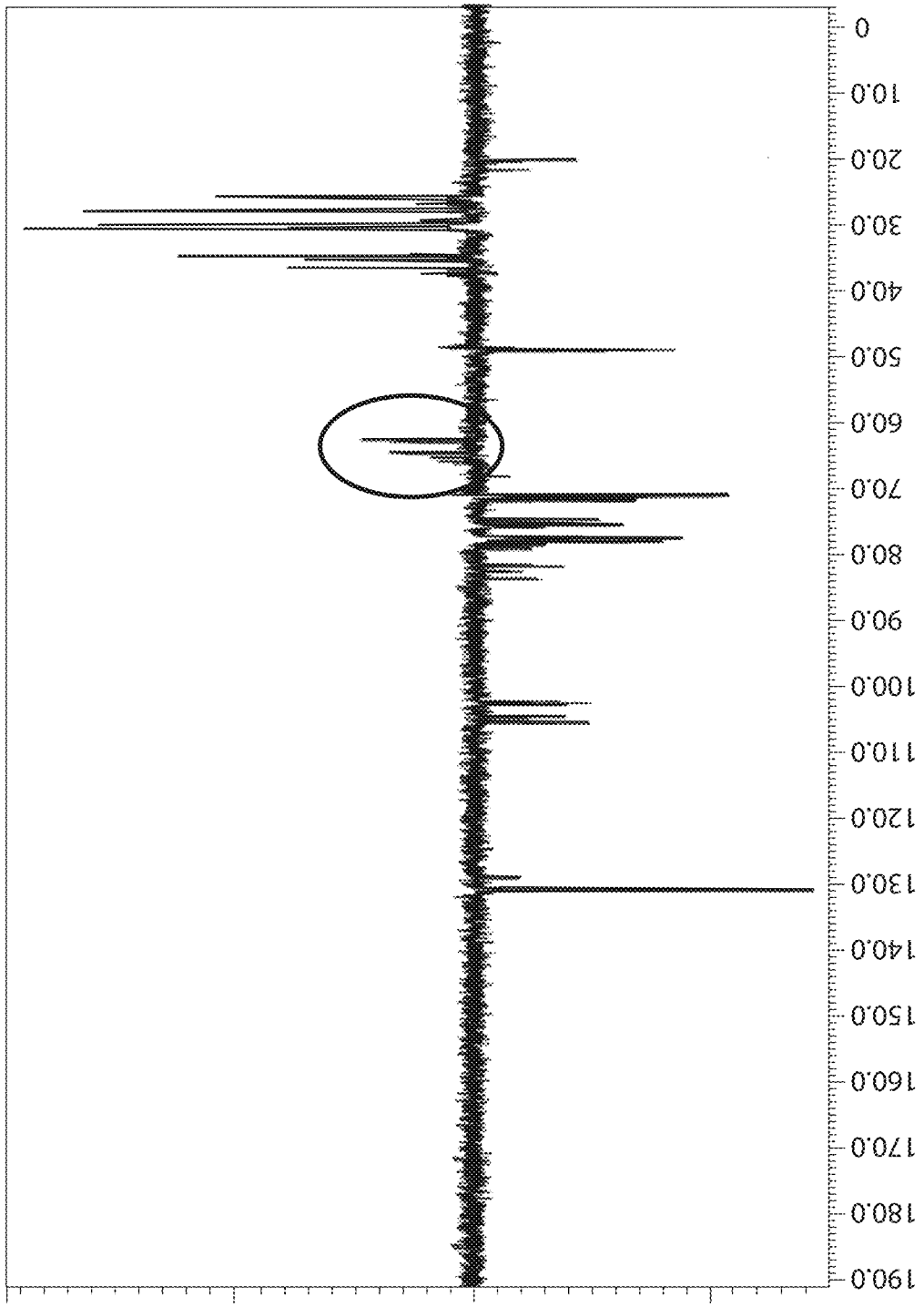
FIGS. 7A-7B show (FIG. 7A) the results of DEPT135 of the novel SL (X1-26) and (FIG. 7B) the results of DEPT135 of the novel SL (X2-36).
Figure 7B:
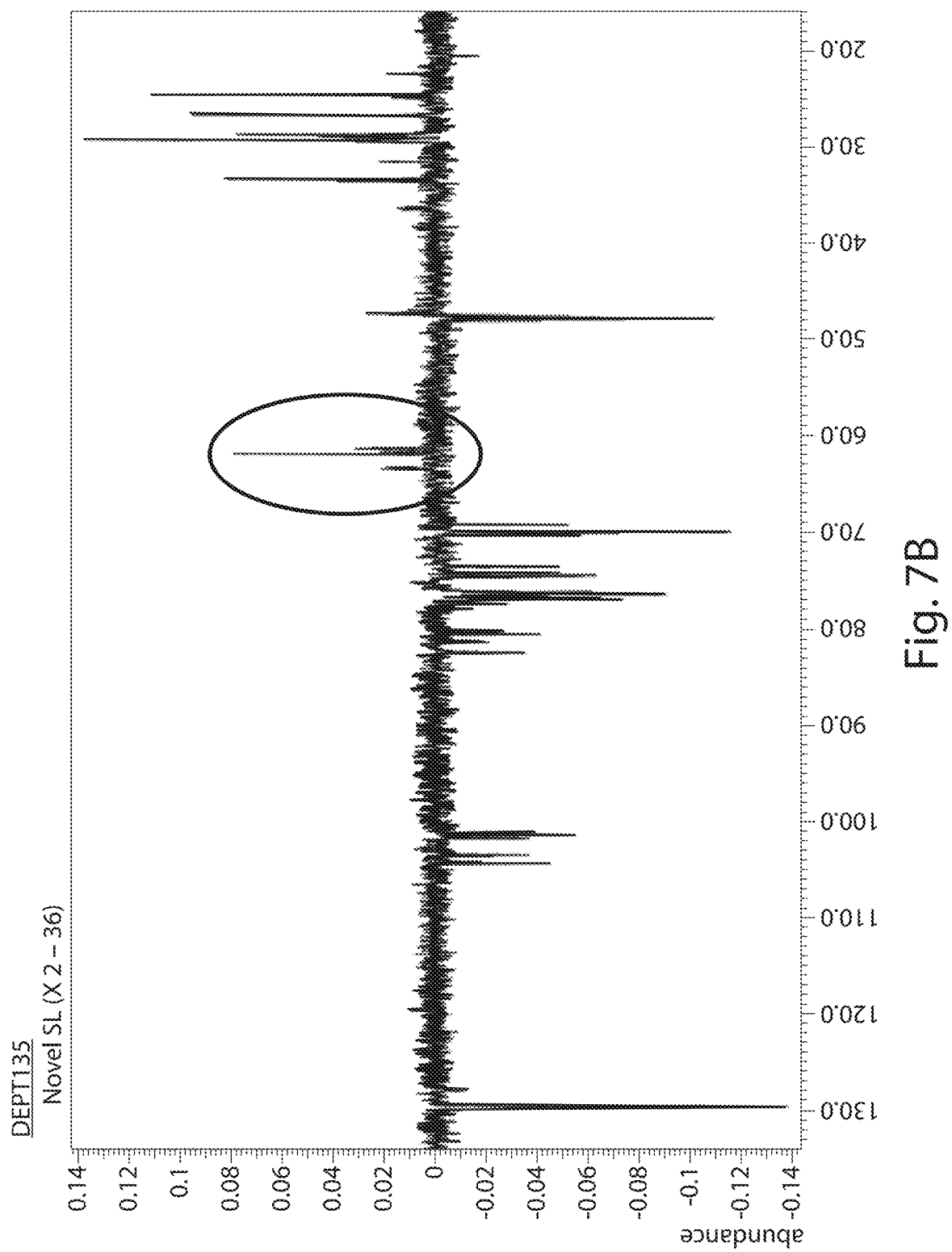

The novel SL (X1-26) and the novel SL (X2-36) were individually subjected to DEPT135 spectrum analysis. FIGS. 7A-7B show the results. As shown in the figures, it was confirmed that C6' and C6" of the sugar skeleton were 64.7 ppm and 64.9 ppm, respectively (denoted by the circles in FIGS. 7A-7B). With the correlation with HMBC (FIG. 4B and FIG. 6B), it was confirmed that acetyl groups are bonded to the C6' and C6" positions of the compound represented by Formula (I). However, a proton is bonded at the C6" position of the novel SL (X2-36). This revealed that acetyl groups are bonded at C6' and C6" of the sophorose ring of the novel SL (X1-26) through ester bonds, and that an OH group and an acetyl group are bonded to C6" and C6' of the sophorose ring of the novel SL (X2-36), respectively, through ester bonds.

(4-5) MS/MS Analysis

Figure 8A:
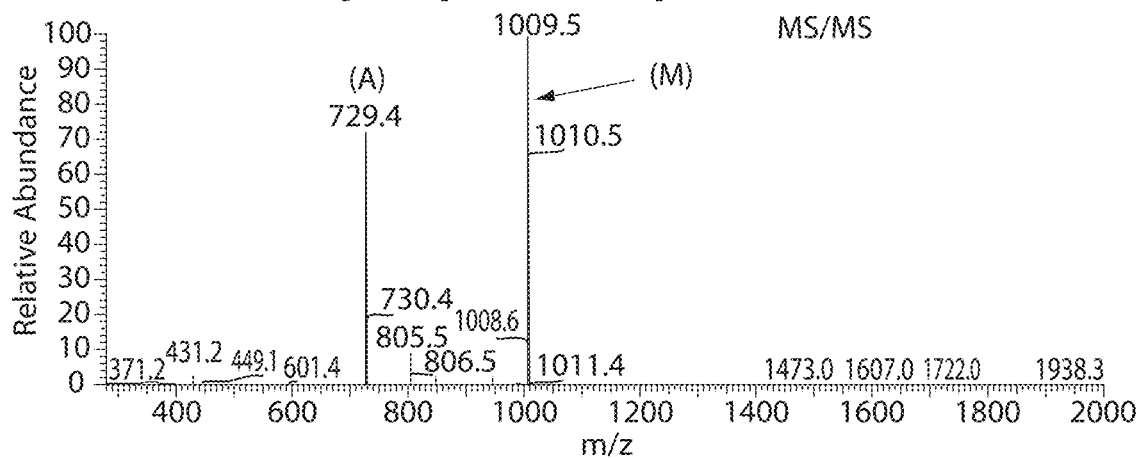
FIGS. 8A-8B show (FIG. 8A) the results of MS$^{(n)}$ analysis (positive mode) of the novel SL (X1-26), and (FIG. 8B) the results of MS$^{(n)}$ analysis (positive mode) of the novel SL (X2-36).
Figure 8A:
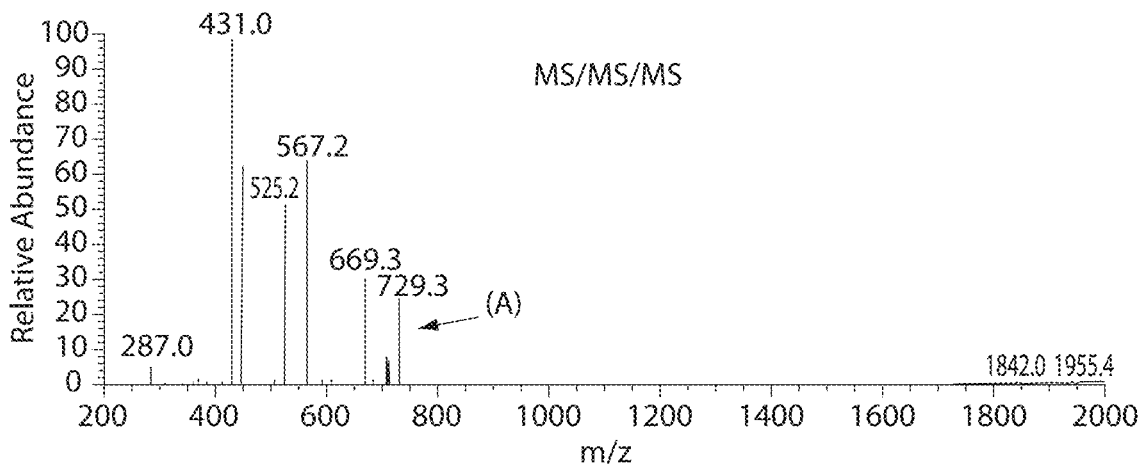
Figure 8B:
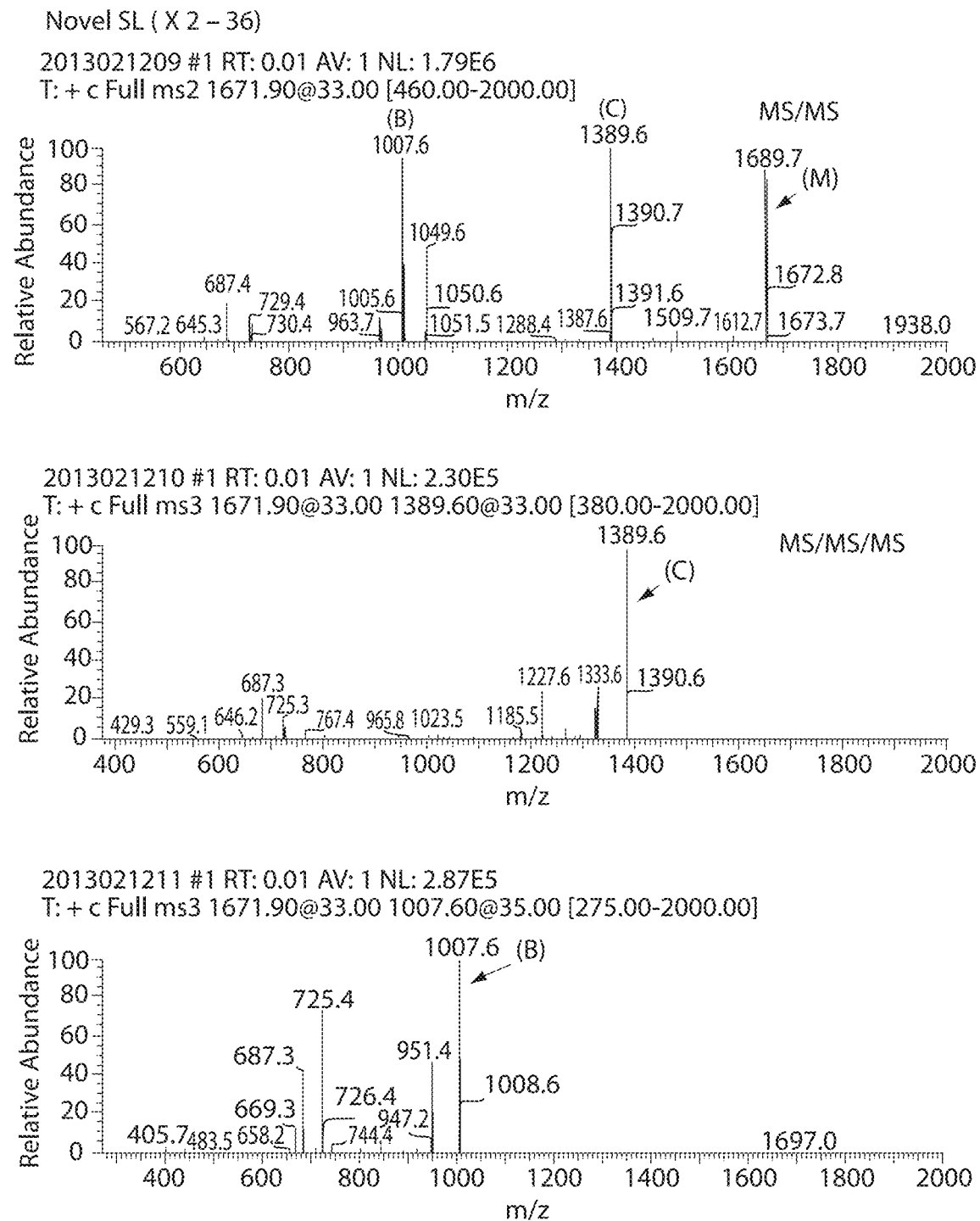

The decomposition products of the novel SL (X1-26) and the novel SL (X2-36) were individually confirmed through $MS^{(n)}$ analysis (positive mode). FIGS. 8A-8B show the mass spectra of the novel SL (X1-26) and the novel SL (X2-36), respectively.

Further, according to FIG. 8A, in the novel SL (X1-26), a daughter ion (A) m/z 729 resulting from decomposition of a compound with a molecular weight of [−280, C18Δ1] from the parent ion (M) was detected. It was revealed that the daughter ion completely matched the conventional SL (acidic SL) (however, it has two acetyl groups), and that a hydroxy oleic acid (C18Δ1) is bonded to the conventional SL (acidic SL).

Further, according to FIG. 8B, in the novel SL (X2-36), daughter ions (B) and (C) resulting from decomposition of compounds with a molecular weight of [−661, acidic SL (C16, Ac1)] and [−280, C18Δ1] from the parent ion (M') were detected. The daughter ion (B) was matched with the molecular weight of the novel SL (X1-26). With this result, it was assumed that the novel SL (X2-36) has a structure in which the novel SL (X1-26) is bonded to a conventional SL (acidic SL) (having one acetyl group). By further decomposing the daughter ion (C), the same value as the pseudo-molecular weight of the conventional SL (acidic SL) was obtained.

(4-6) Hydrolysis

20 μL of 48 mass % sodium hydroxide and 1.88 mL of distilled water were added to the mixture (0.1 g) of the X1 fraction and the X2 fraction, and the resulting mixture was heated for two hours at 80° C. After the mixture was cooled to room temperature, 3 mL of hexane was added. After sufficient mixing, the mixture was centrifuged, the hexane layer was isolated, and the fatty acids were removed. This step (hexane extraction) was repeated three times. The aqueous layer from which the fatty acids were removed was subjected to HPLC analysis. The results confirmed detection of a peak of a conventional acidic SL (however, no acetyl group), thereby confirming that the fatty acid residue represented by $R_5$ in Formula (I) is bonded to the sophorose ring through an ester bond.

The above results (4-1) to (4-6) confirmed that the novel SL (X1-26) has, as shown in Formula (III) below, a backbone of a conventional acidic SL and is structured such that a hydroxy oleic acid residue, which is a $C_{18}$ monovalent unsaturated fatty acid having hydroxy, is bonded at the C4"-position of the sophorose ring through an ester bond. Further, since each proton at the C6' and C6"-position is coupled with carbonyl from an acetyl group, it was confirmed that acetyl groups are bonded both to C6' and 6"-positions of the sophorose ring via oxygen atoms. Since these acetyl group are easily hydrolyzed, they are decomposed over time, and become hydrogen atoms.

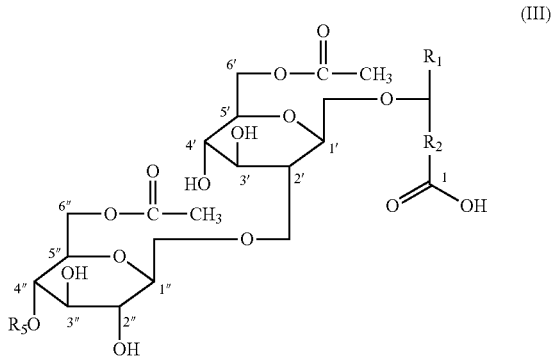

(in Formula (III), $R_1$ represents a methyl group, $R_2$ represents a $C_{15}$ alkenylene group, and $R_5$ represents an oleic acid residue having hydroxy)

Further, the novel SL (X2-36) has, as shown in Formula (IV) below, a backbone of a conventional acidic SL and is structured such that a hydroxy oleic acid residue, which is a $C_{18}$ monovalent unsaturated fatty acid having hydroxy, is bonded at the C4"-position of the sophorose ring through an ester bond. Further, since each proton at the C6'-position and the C6"-position is coupled with carbonyl from the acetyl group, it was confirmed that acetyl groups are bonded both to the C6' and 6"-positions of the sophorose ring via oxygen atoms. As in the novel SL (X1-26), since the acetyl groups are easily hydrolyzed, they are decomposed over time, and become hydrogen atoms. It was further confirmed that the novel SL (X2-36) was a dimer in which the acidic SL represented by Formula (V) below is bonded at the C-1-position.

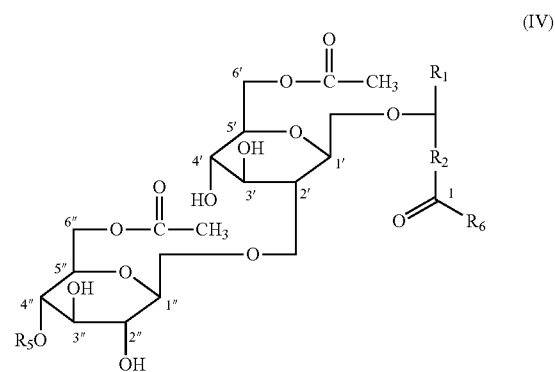

(in Formula (IV), $R_1$ represents a methyl group, $R_2$ represents a $C_{15}$ alkenylene group, $R_5$ represents an oleic acid residue having hydroxy, and $R_6$ forms a single bond together with $R_7$ in Formula (V) below)

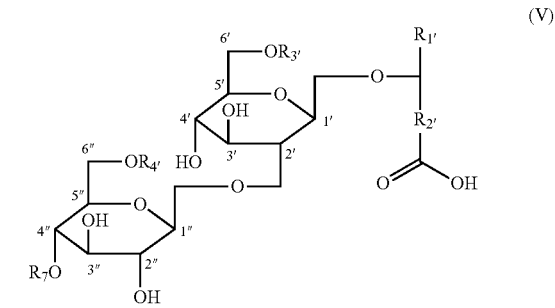

(in Formula (V), $R_{1'}$ represents a methyl group, $R_{2'}$ represents a $C_{13}$ alkylene group, $R_{3'}$ represents a hydrogen atom, and $R_{4'}$ represents an acetyl group).

(4-7) MALDI/TOF MS Analysis

Figure 9A:
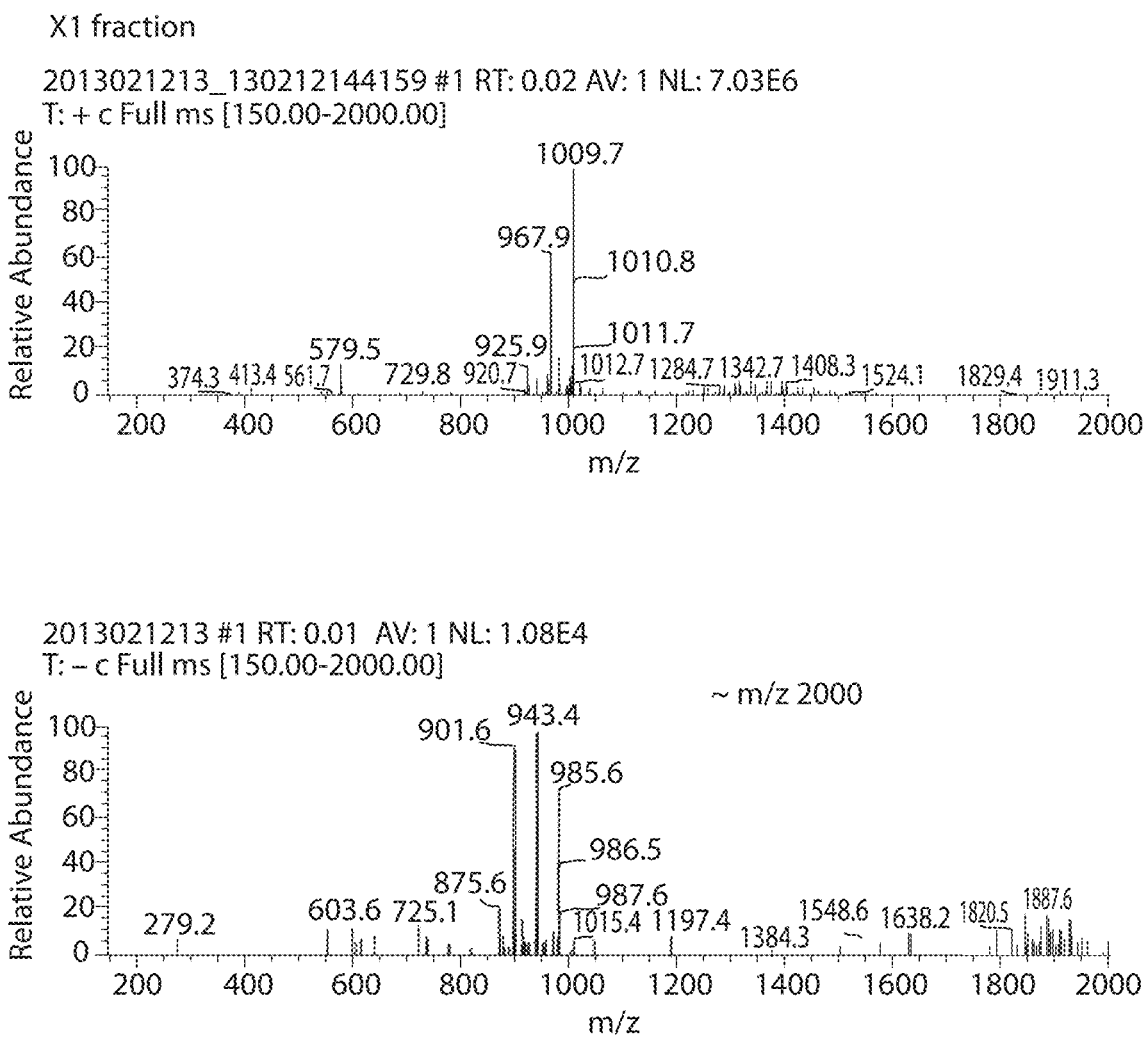
FIGS. 9A-9B show (FIG. 9A) results of ESI-MS analysis of an X1 fraction, and (FIG. 9B) the results of ESI-MS analysis of an X2 fraction.
Figure 9B:
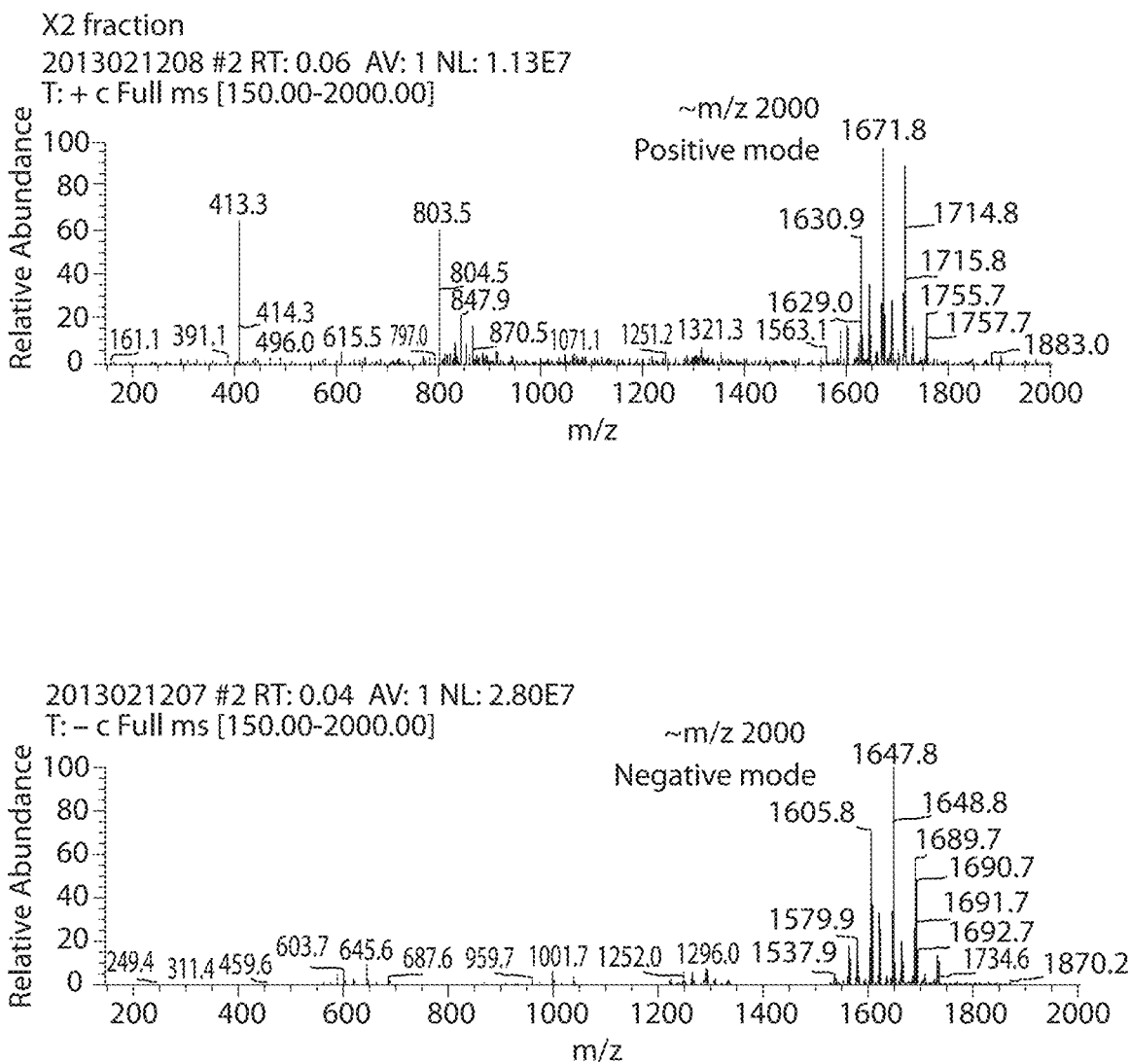

The X1 fraction and the X2 fraction were individually subjected to MALDI/TOF MS analysis under the following conditions, thereby confirming the molecular weights.
Device: AXIMA Confidence (Shimazdu Co.)
Mode: Linear (positive)
Matrix: DHBA FIGS. 9A-9B show the results of the X1 fraction and the X2 fraction, respectively. With these results, the molecular weights were calculated, and the number of the bonded acetyl groups was confirmed. Tables 5 and 6 show the results.

TABLE 5

X1 Fraction

| Detected Peaks | Number of Carbon Atoms in $R_5$ | Number of Carbon Atoms in $R_2$ | Number of Acetyl Groups ($R_3$ or $R_4$) |
|---|---|---|---|
| 899 | C16 | C13 | 1 |
| 925 | C16 | C15Δ1 | 1 |
| 927 | C16 | C15 | 1 |
| 941 | C18Δ1 | C13 | 1 |
| 943 | C16 | C15 | 1 |
| 957 | C14 | C15 | 2 |
| 966 | C18Δ2 | C15 | 1 |
| 967 | C18Δ1 | C15Δ1 | 1 |
| 969 | C18 | C13 | 2 |
| 981 | C16 | C15Δ2 | 2 |
| 983 | C16 | C15Δ1 | 2 |
| 999 | C18 | C15 | 2 |
| 1009 | C18Δ1 | C15Δ1 | 2 |
| 1023 | C20 | C15Δ1 | 2 |
| 1025 | C20 | C15 | 2 |

The results confirmed that the X1 fraction contained 14 compounds having an SL structure and the above groups, in addition to the compound (X1-26) (detection peak: 1009) represented by Formula (III). More specifically, as shown in the above table, these 14 kinds of compounds are assumed to have a structure in which a $C_{16-20}$ saturated or unsaturated fatty acid residue that may have hydroxy is bonded either at the 2", 3", 4", 3', or 4'-position of the sophorose ring of a conventional acidic SL through an ester bond.

TABLE 6

X2 Fraction

| Detected Peaks | Number of Carbon Atoms in $R_5$ | Number of Carbon Atoms in $R_2$ | Number of Carbon Atoms in $R_{2'}$ | Number of Acetyl Groups ($R_4$, $R_5$, $R_{4'}$, $R_{5'}$) |
|---|---|---|---|---|
| 1587 | C14 | C15 | C15Δ1 | 4 |
| 1589 | C12 | C15Δ2 | C13 | 4 |
| 1603 | C16 | C13 | C13Δ1 | 3 |
| 1605 | C16 | C13 | C15 | 3 |
| 1629 | C18Δ1 | C15Δ1 | C13 | 3 |
| 1630 | C18Δ1 | C15 | C13 | 3 |
| 1645 | C14 | C15 | C15Δ1 | 4 |
| 1647 | C16 | C13 | C15 | 4 |
| 1671 | C18Δ1 | C15Δ1 | C13 | 3 |
| 1672 | C16 | C13 | C15Δ1 | 4 |
| 1688 | C18 | C15 | C15 | 4 |
| 1713 | C20 | C15 | C15Δ1 | 4 |
| 1715 | C20 | C15 | C15 | 4 |
| 1725 | C20 | C15Δ2 | C15Δ1 | 4 |
| 1726 | C20 | C15Δ1 | C15Δ1 | 4 |
| 1728 | C20 | C15 | C15Δ1 | 4 |

The results confirmed that the X2 fraction contained 15 compounds having an SL structure and the above groups, in addition to the compound (X2-36) (detection peak: 1671) represented by Formula (IV). More specifically, as shown in the above table, these 15 kinds of compounds are assumed to be dimers having a structure in which a $C_{12-20}$ saturated or unsaturated fatty acid residue that may have hydroxy is bonded either at the 2", 3", 4", 3', or 4'-position of the sophorose ring of a conventional acidic SL through an ester bond, and the $R_6$ group in Formula (I) forms a single bond together with $R_7$ bonded at the 4"-position of the sophorose ring in Formula (II) via an oxygen atom. Examples of $R_{2'}$ in Formula (II) include a $C_{13-15}$ alkylene group and a $C_{15}$ alkenylene group having 1 or 2 double bonds. In other words, the compound contained in the X2 fraction is a dimer in which the C1-position of the compound represented by Formula (I) is bonded to the 4"-position of the conventional acidic SL ($R_{2'}$ is C16, C18, C18Δ1, C18Δ2) through an ester bond.

(4-8) ESI-MS Analysis $MS^{(n)}$ analysis was performed under the following conditions so as to confirm the molecules (units) of the X1 fraction and the X2 fraction.

TABLE 7

MS Analysis Conditions

| Device | LCQDECA (Thermo Quest) |
|---|---|
| Ionization Mode | ESI(+, −) |
| Capillary Temperature | 310° C. |
| Sheath Gas Amount | 80 Units |
| Spray Voltage | 5 kV |

Figure 10A:
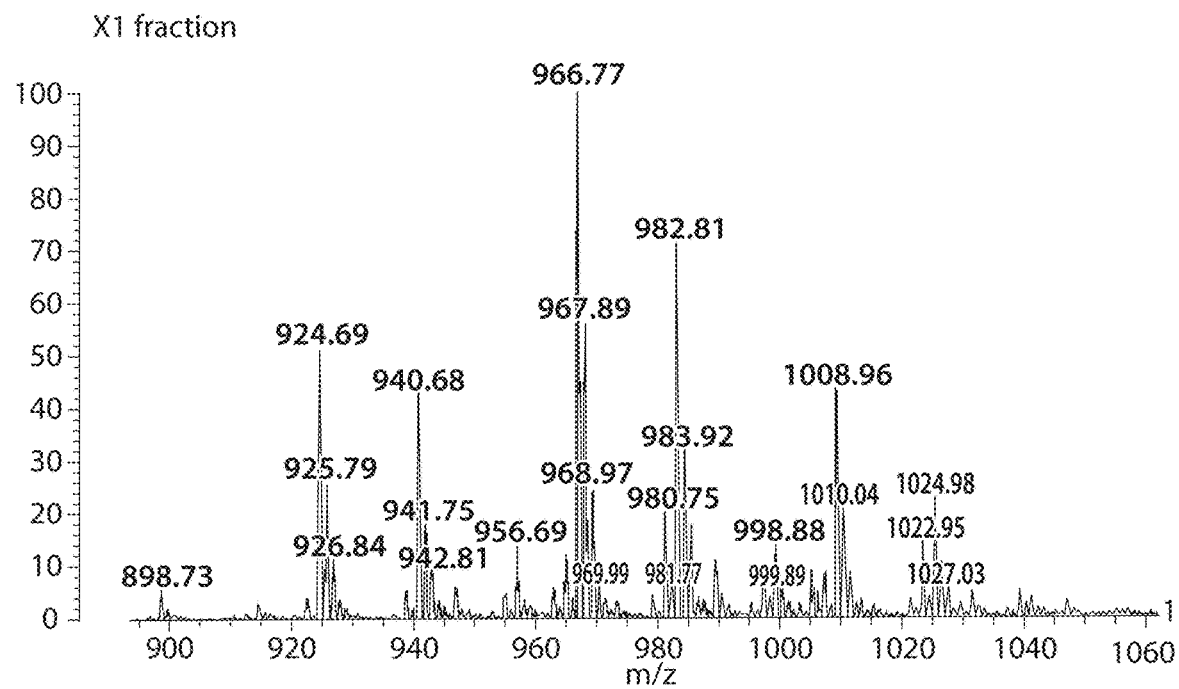
FIGS. 10A-10B show (FIG. 10A) the results of MALDI/TOF MS analysis of the X1 fraction, and (FIG. 10B) the results of MALDI/TOF MS analysis of the X2 fraction.
Figure 10B:
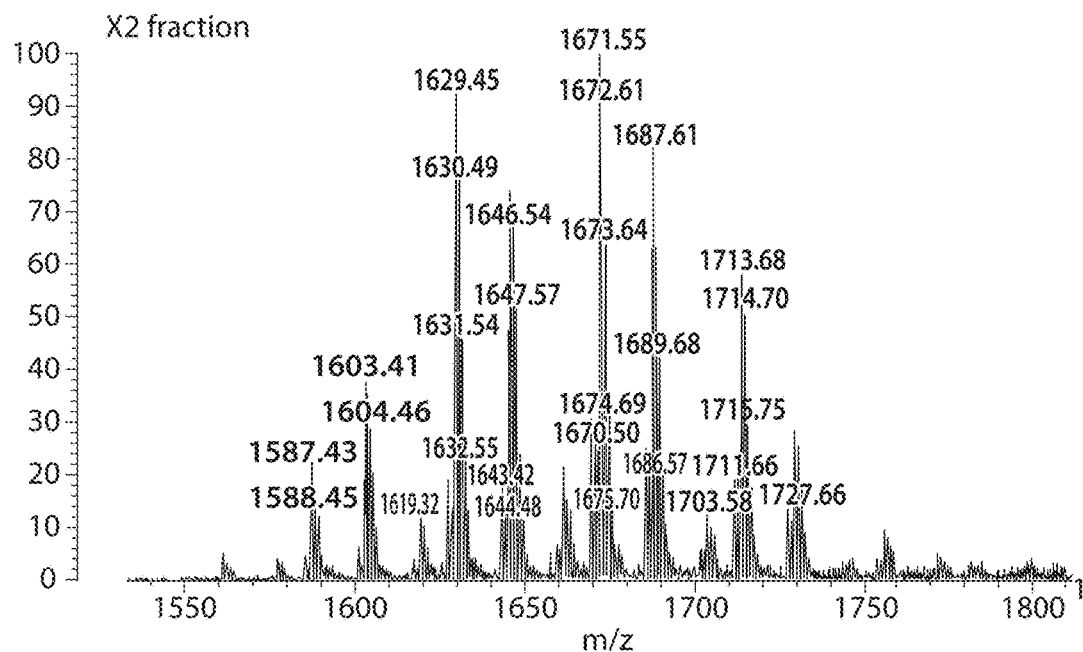

FIGS. 10A-10B show the mass spectra of the X1 fraction and the X2 fraction, respectively. With these results, the molecular weights of the compounds contained in the X1 fraction and the X2 fraction were calculated. Table 8 shows the results. As shown in the table, the molecular weights obtained by ESIMS were similar to those obtained by MALDI/TOF MS.

TABLE 8

Molecular Weights of Compounds Contained in X1 Fraction and X2 Fraction (Example)

| Elution Time (Minutes) | X1 | X2 |
|---|---|---|
| Positive Mode | 925, 967, 1009 | 1671, 1714 |
| Negative Mode | 901, 943, 985 | 1647, 1689 |
| Molecular Weight | 902, 944, 986 | 1648, 1690 |

Test Example 1

Surfactant Performance

The surfactant performances of the monomeric SL compound (X1 fraction) and the dimeric SL compound (X2 fraction) identified above were individually evaluated both in terms of surface tension and emulsifying capacity.

(1) Surface Tension

Each of the monomeric SL compound and the dimeric SL compound was prepared into a 0.1 mass % aqueous solution, and the minimum surface tension (mN/m) was measured using the Wilhelmy method (20° C., pH 7). For comparison, the minimum surface tension of a conventional SL (acidic SL), which has already been used as a surfactant, was also measured.

The conventional SL (acidic SL) is a compound having a structure in which $R_1$ is a methyl group, $R_2$ is a $C_{15}$ alkenylene group, and $R_3$ and $R_4$ are acetyl groups, in the chemical formula represented by Formula (VI) (the same in Test Example 2 below).

Table 9 shows the results. As is clear from the results, both the monomeric SL compound and the dimeric SL compound had surface tension equivalent to that of the conventional SL (acidic SL).

TABLE 9

| | Minimum Surface Tension (mN/m) |
|---|---|
| Conventional SL (Acidic SL) | 40.2 |
| Monomeric SL Compound | 39.9 |
| Dimeric SL Compound | 39.1 |

(2) Emulsifying Capacity

The monomeric SL compound or the dimeric SL compound was added to distilled water, and the mixture was adjusted to pH 7 using sodium hydroxide (the final concentration of the monomeric SL compound or the dimeric SL compound was 2 mass %), and heated to 80° C. 3 g of this sample and 3 g of olive squalane were placed in a 15 mL centrifuge tube, and heated at 80° C. for 10 minutes. Thereafter, the mixture was stirred with a vortex for a minute. The volume of water separated at a certain interval at room temperature was measured by visual inspection, and recorded. The water separation ratio was found according to the formula below to evaluate emulsifying capacity (n=2). For comparison, the emulsifying capacity of a conventional SL (acidic SL), which has already been used as a surfactant, was also measured. Table 10 shows the results. As is clear from the results, both the monomeric SL compound and the dimeric SL compound had emulsifying capacity equivalent to that of the conventional SL (acidic SL).

$$\text{Water separation ratio} = \frac{\text{amount of water seperated}}{\text{amount of water used}} \times 100 \quad [\text{Math 1}]$$

TABLE 10

| Time | 1 | 3 | 6 | 24 | 48 |
|---|---|---|---|---|---|
| Conventional SL (Acidic SL) | 55 | 54 | 54 | 54 | 54 |
| Monomeric SL Compound | 54 | 54 | 54 | 54 | 54 |
| Dimeric SL Compound | 54 | 54 | 54 | 54 | 54 |

Unit (%)

As is clear from the results, it was confirmed that both the monomeric SL compound and the dimeric SL compound had surfactant performance (surface tension, emulsifying capacity) equivalent to that of the conventional acidic SL.

Test Example 2

Sensory Evaluation (Bitterness) 1

With 20 healthy test subjects (panelists), the intensity of the bitterness of the conventional SL (acidic SL, lactonic SL), the monomeric SL compound, and the dimeric SL compound was measured. Each test sample was prepared into an aqueous solution (pH=7) at a concentration of 0.5 mass % by being dissolved in water. Each panelist compared the taste of each test sample with the taste of aqueous solutions of a standard substance at various concentrations, and selected a standard substance aqueous solution (concentration) having the same bitterness as that of the test sample. "L-tryptophan (Kyowa Hakko Kogyo Co., Ltd., Lot No. S860281)" was used as the reference substance for evaluating bitterness. An aqueous solution having a concentration of 0.05 to 0.25 mass % was prepared as a low-concentration aqueous solution, and an aqueous solution having a concentration of 0.5 to 1.0 mass % was prepared as a high-concentration aqueous solution.

The conventional SL (lactonic SL) is a compound having a structure in which $R_1$ is a methyl group, $R_2$ is a $C_{15}$ alkenylene group, and $R_3$ and $R_4$ are acetyl groups, in the chemical formula represented by Formula (VII).

Tables 11 to 14 show the results.

TABLE 11

| Monomeric SL Compound (X1 Fraction) | | | | | | | |
|---|---|---|---|---|---|---|---|
| | Concentration of Reference Substance (%) | | | | | | |
| | 0 | 0.05 | 0.1 | 0.15 | 0.2 | 0.25 | Average* |
| Respondent (Person) | 0 | 8 | 7 | 5 | 0 | 0 | 0.093 |

Calculation of Average $$(0 \times 0 + 0.05 \times 8 + 0.1 \times 7 + 0.15 \times 5 + 0.2 \times 0 + 0.25 \times 0)/20 = 0.093$$

TABLE 12

| Dimeric SL Compound (X2 Fraction) | | | | | | | |
|---|---|---|---|---|---|---|---|
| | Concentration of Reference Substance (%) | | | | | | |
| | 0 | 0.05 | 0.1 | 0.15 | 0.2 | 0.25 | Average* |
| Respondent (Person) | 0 | 9 | 7 | 4 | 0 | 0 | 0.088 |

Calculation of Average $$(0 \times 0 + 0.05 \times 9 + 0.1 \times 7 + 0.15 \times 4 + 0.2 \times 0 + 0.25 \times 0)/20 = 0.088$$

TABLE 13

| Conventional SL (Lactonic SL) | | | | | | | |
|---|---|---|---|---|---|---|---|
| | Concentration of Reference Substance (%) | | | | | | |
| | 0.5 | 0.6 | 0.7 | 0.8 | 0.9 | 1 | Average* |
| Respondent (Person) | 9 | 8 | 2 | 1 | 0 | 0 | 0.575 |

Calculation of Average $$(0.5 \times 9 + 0.6 \times 8 + 0.7 \times 2 + 0.8 \times 1 + 0.9 \times 0 + 1 \times 0)/20 = 0.575$$

TABLE 14

| Conventional SL (Acidic SL) | | | | | | | |
|---|---|---|---|---|---|---|---|
| | Concentration of Reference Substance (%) | | | | | | |
| | 0.5 | 0.6 | 0.7 | 0.8 | 0.9 | 1 | Average* |
| Respondent (Person) | 0 | 2 | 6 | 5 | 7 | 0 | 0.785 |

Calculation of Average (0.5×0+0.6×2+0.7×6+0.8×5+0.9×7+1×0)/20=0.785

As is clear from the results, the aqueous solutions (pH=7) of the acidic conventional SL at a concentration of 0.5 mass % both had bitterness substantially equivalent to that of a 0.785 mass % L-tryptophan aqueous solution, whereas the aqueous solutions (pH=7) of the monomeric SL compound and the dimeric SL compound at a concentration of 0.5 mass % had bitterness substantially equivalent to that of a 0.093 mass % L-tryptophan aqueous solution and a 0.088 mass % L-tryptophan aqueous solution, respectively. The results thus revealed that the bitterness of the monomeric SL compound and the dimeric SL compound was, compared to that of the conventional SL, reduced 8- to 10-fold.

Test Example 3

Sensory Evaluation (Bitterness) 2

The various products were produced according to the formulations below, and the presence/absence of bitterness was evaluated for each product by a sensory test.

Formulation Example 1: Cookie

TABLE 15

| Material | Mass % |
| --- | --- |
| SL (Conventional SL (Acidic SL), Monomeric SL Compound or Dimeric SL Compound) | 1.0 |
| Soft Wheat Flour | 52.1 |
| Cooking Oil | 20.8 |
| Sugar | 20.8 |
| Water | 5.2 |

The materials in the above formulation were mixed, shaped into cookies, and baked at 180° C. for 13 minutes, thereby producing cookies. The panelists ate the cookies, and evaluated the presence/absence of the bitterness in comparison with cookies produced without adding SL (control). The results revealed that the cookies containing the conventional SL (acidic SL) had strong bitterness, whereas the cookies containing the SL compound of the present invention, i.e., the monomeric SL compound or the dimeric SL compound, had no bitterness, thereby confirming that both the monomeric SL compound and the dimeric SL compound have no effect on the taste of food.

Formulation Example 2: Cosmetics (Lip Balm) pH=6

TABLE 16

| Raw Material | Mass % |
| --- | --- |
| Beeswax | 30 |
| Shea Fat | 20 |
| Polyglyceryl-2 Isostearate/Dimer Dilinoleic Acid Copolymer | 10 |
| Olive Squalane | 28 |
| Glycerin | 5 |
| Water | 5.8 |
| SL (Conventional SL (Acidic SL), Monomeric SL Compound or Dimeric SL Compound) | 0.5 |
| Citric Sodium | 0.5 |
| Citric Acid | 0.2 |

The aqueous components and the oil components in the above formulation were heated individually to 80° C. to 90° C. according to a usual method, and the components were mixed and stirred. The resulting mixture was returned to room temperature, thereby producing a lip balm. The panelists applied the lip balm on their lips, and evaluated whether they felt bitterness on the tip of the tongue when they licked their lips, in comparison with a lip balm produced without adding SL (control). The results revealed that the lip balm containing the conventional SL (acidic SL) had strong bitterness, whereas the lip balm containing the SL compound of the present invention, i.e., the monomeric SL compound or the dimeric SL compound, had no bitterness, thereby confirming that both the monomeric SL compound and the dimeric SL compound have no effect on the taste of the product (lip balm).

Formulation Example 3: Lotion (pH=4 or 9)

TABLE 17

| Raw Material | Mass % |
| --- | --- |
| BG | 7 |
| SL (Conventional SL (Acidic SL), Monomeric SL Compound or Dimeric SL Compound) | 0.5 |
| Glycerin | 5 |
| Xanthan Gum | 0.1 |
| 1,2-Hexanediol | 1 |
| pH Adjuster (Potassium Hydroxide) | Use appropriate amount to adjust pH to 4 or 9 |
| Water | Balance |

The components in the above formulation were mixed, thereby producing lotions respectively having a pH of 4 and 9. The panelists applied the lotions on their skin (including lips), and evaluated whether they felt bitterness on the tip of the tongue when they licked their lips, in comparison with a lip balm produced without adding SL (control). The results revealed that the lip balm containing the conventional SL (acidic SL) had strong bitterness, whereas the lip balm containing the SL compound of the present invention, i.e., the monomeric SL compound or the dimeric SL compound, had no bitterness, thereby confirming that both the monomeric SL compound and the dimeric SL compound have no effect on the taste of the product (lotion).

Formulation Example 4: Emulsion (pH=3 to 9)

TABLE 18

| Raw Material | Mass % |
| --- | --- |
| Monomeric SL Compound or Dimeric SL Compound | 5 |
| Glycerin | 5 |
| Carbomer | 0.3 |
| Phenoxy Ethanol | 0.95 |
| Squalane | 3 |
| pH Adjuster (Potassium Hydroxide) | Use appropriate amount to adjust pH to 3 to 9 |
| Water | Balance |

The materials in the above formulation were mixed according to a usual method, thereby preparing an emulsion with no bitterness.

Formulation Example 5: Cream for External Use (pH=3 to 9)

TABLE 19

| Raw Material | Mass % |
| --- | --- |
| Monomeric SL Compound or Dimeric SL Compound | 10 |
| Glycerin | 5 |
| Carbomer | 0.5 |
| Phenoxy Ethanol | 0.95 |
| Squalane | 5 |
| Cetanol | 2 |
| pH Adjuster (Potassium Hydroxide) | Use appropriate amount to adjust pH to 3 to 9 |
| Water | Balance |

The materials in the above formulation were mixed according to a usual method, thereby preparing a cream for external use with no bitterness.

Formulation Example 6: Liquid Facial Wash (pH=3 to 9)

TABLE 20

| Raw Material | Mass % |
| --- | --- |
| Monomer SL Compound or Dimeric SL Compound | 30 |
| Glycerin | 10 |
| Phenoxy Ethanol | 0.95 |
| pH Adjuster (Potassium Hydroxide) | Use appropriate amount to adjust pH to 3 to 9 |
| Water | Balance |

The materials in the above formulation were mixed according to a usual method, thereby preparing a facial wash with no bitterness.

Formulation Example 7: Liquid Facial Cleansing (pH=3 to 9)

TABLE 21

| Raw Material | Mass % |
| --- | --- |
| Monomeric SL Compound or Dimeric SL Compound | 10 |
| Glycerin | 10 |
| Phenoxy Ethanol | 0.95 |
| pH Adjuster (Potassium Hydroxide) | Use appropriate amount to adjust pH to 3 to 9 |
| Water | Balance |

The materials in the above formulation were mixed according to a usual method, thereby preparing a liquid facial cleansing with no bitterness.

The invention claimed is:

1. A sophorolipid compound represented by Formula (I):

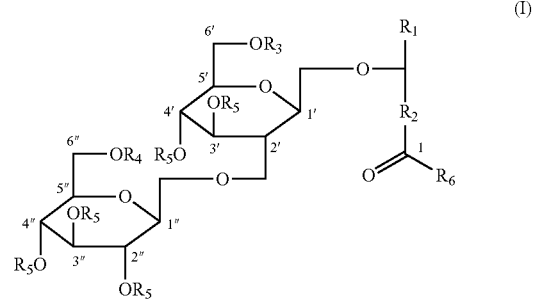

wherein: $R_1$ represents a hydrogen atom or methyl group; $R_3$ and $R_4$ are the same or different, and each represents a hydrogen atom or acetyl group; one of five $R_5$ is a saturated or unsaturated fatty acid residue that may have hydroxy, and the remaining four $R_5$ are hydrogen atoms; $R_2$ represents a $C_{9-18}$ alkylene group, or $C_{9-18}$ alkenylene group having 1 to 3 double bonds; and $R_6$ represents hydroxy, or may form a single bond together with one of five $R_7$ in the compound represented by Formula (II):

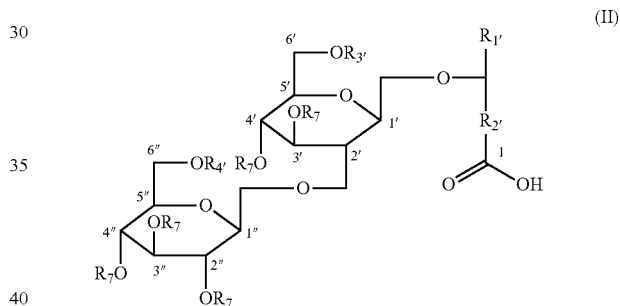

wherein: $R_{1'}$ represents a hydrogen atom or methyl group; $R_{3'}$ and $R_{4'}$ are the same or different, and each represents a hydrogen atom or acetyl group; $R_{2'}$ represents a $C_{9-18}$ alkylene group, or $C_{9-18}$ alkenylene group having 1 to 3 double bonds; and one of $R_7$ forms a single bond together with $R_6$ in the compound represented by Formula (I) and the remaining four $R_7$ are hydrogen atoms.

2. The sophorolipid compound according to claim 1, wherein: $R_6$ is hydroxy; $R_1$ is a methyl group; $R_2$ is a $C_{9-17}$ alkylene group or $C_{13-17}$ alkenylene group having 1 to 3 double bonds; $R_3$ and $R_4$ are the same or different, and each represents a hydrogen atom or acetyl group; and $R_5$ of the $R_5O$-group bonded at the 4"-position of the sophorose ring is a $C_{12-20}$ fatty acid residue that may have or may not have hydroxy, and the remaining $R_5$ are hydrogen atoms.

3. The sophorolipid compound according to claim 1, wherein: $R_6$ is hydroxy; $R_1$ is a methyl group; $R_2$ is a $C_{15}$ alkenylene group having one double bond; $R_3$ and $R_4$ are the same or different, and each represents a hydrogen atom or acetyl group; and $R_5$ of the $R_5O$-group bonded at the 4"-position of the sophorose ring is an oleic acid residue having hydroxy, and the remaining $R_5$ are hydrogen atoms.

4. The sophorolipid compound according to claim 1, wherein the sophorolipid compound is a compound represented by Formula (III):

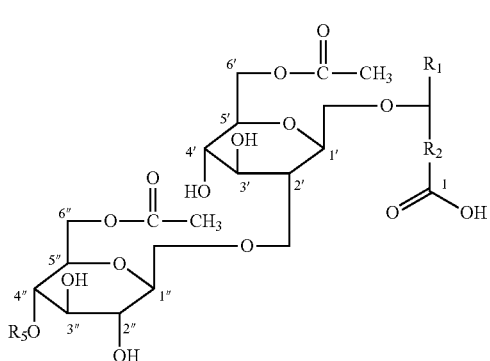

(III)

wherein: $R_1$ represents a methyl group; $R_2$ represents a $C_{15}$ alkenylene group; and $R_5$ represents an oleic acid residue having hydroxyl.

5. A composition comprising at least one sophorolipid compound according to claim 1.

6. The composition according to claim 5, wherein the composition is a surfactant.

7. The composition according to claim 5, wherein the composition is a pharmaceutical, a quasi-drug, a cosmetic, a food or beverage, or an additive thereof.

8. The sophorolipid compound according to claim 1, wherein: $R_6$ forms a single bond together with $R_7$ of the $R_7O$-group bonded at the 4"-position of the sophorose ring in Formula (II); $R_1$ is a methyl group; $R_2$ is a $C_{9-17}$ alkylene group, or $C_{13-17}$ alkenylene group having 1 to 3 double bonds; $R_3$ and $R_4$ are the same or different, and each represents a hydrogen atom or acetyl group; and $R_5$ of the $R_5O$-group bonded at the 4"-position of the sophorose ring is a $C_{12-20}$ fatty acid residue that may have or may not have hydroxy, and the remaining $R_5$ are hydrogen atoms; and, in Formula (II): $R_{1'}$ is a methyl group; $R_{2'}$ is a $C_{9-17}$ alkylene group, or $C_{13-17}$ alkenylene group having 1 to 3 double bonds; and $R_{3'}$ and $R_{4'}$ are the same or different, and each represents a hydrogen atom or acetyl group.

9. The sophorolipid compound according to claim 1, wherein: $R_6$ forms a single bond together with $R_7$ of the $R_7O$-group bonded at the 4"-position of the sophorose ring in Formula (II); $R_1$ is a methyl group; $R_2$ is a $C_{15}$ alkenylene group having one double bond; $R_3$ and $R_4$ are the same or different, and each represents a hydrogen atom or acetyl group; $R_5$ of the $R_5O$-group bonded at the 4"-position of the sophorose ring is an oleic acid residue having hydroxy, and the remaining $R_5$ are hydrogen atoms; and, in Formula (II): $R_{1'}$ is a methyl group; $R_{2'}$ is a $C_{13}$ alkylene group; and $R_{3'}$ and $R_{4'}$ are the same or different, and each represents a hydrogen atom or acetyl group.

10. The sophorolipid compound according to claim 1, wherein the sophorolipid compound is a compound represented by Formula (IV):

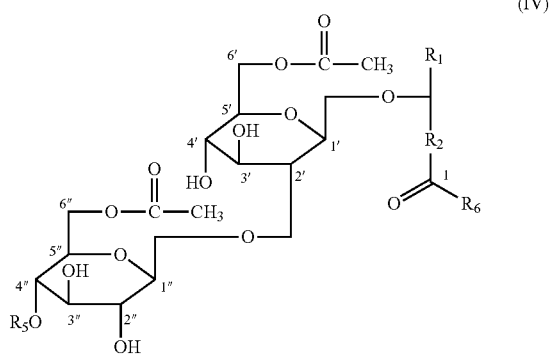

(IV)

wherein: $R_1$ represents a methyl group; $R_2$ represents a $C_{15}$ alkenylene group; $R_5$ represents an oleic acid residue having hydroxyl; and $R_6$ forms a single bond together with $R_7$ in Formula (V):

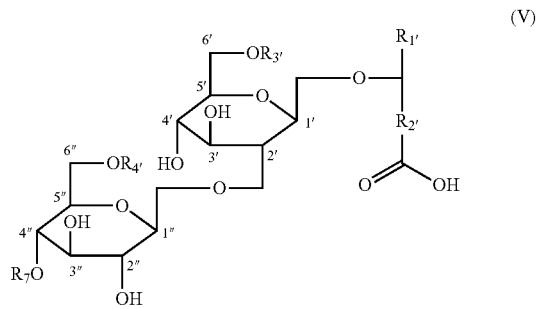

(V)

wherein: $R_{1'}$ represents a methyl group; $R_{2'}$ represents a $C_{13}$ alkylene group; $R_{3'}$ represents a hydrogen atom; and $R_{4'}$ represents an acetyl group.

* * * * *